(12) United States Patent
Njemanze

(10) Patent No.: US 8,152,727 B2
(45) Date of Patent: Apr. 10, 2012

(54) METHOD FOR ASSESSMENT OF COLOR PROCESSING MECHANISM IN THE HUMAN BRAIN FOR DIAGNOSIS AND TREATMENT

(75) Inventor: Philip Chidi Njemanze, Owerri (NG)

(73) Assignee: Chidicon Medical Center, Owerri Imo State (NG)

( * ) Notice: Subject to any disclaimer, the term of this patent is extended or adjusted under 35 U.S.C. 154(b) by 1520 days.

(21) Appl. No.: 11/636,554

(22) Filed: Dec. 11, 2006

(65) Prior Publication Data

US 2008/0139941 A1    Jun. 12, 2008

(51) Int. Cl.
*A61B 8/06* (2006.01)
*A61B 5/00* (2006.01)

(52) U.S. Cl. .......................... 600/454; 600/558
(58) Field of Classification Search .......... 600/452–457, 600/558; 351/242
See application file for complete search history.

(56) References Cited

U.S. PATENT DOCUMENTS

| | | | |
|---|---|---|---|
| 3,653,771 A * | 4/1972 | Piringer | 356/422 |
| 3,801,188 A * | 4/1974 | Hunt et al. | 351/237 |
| 3,947,099 A * | 3/1976 | Grolman et al. | 351/242 |
| 3,970,376 A * | 7/1976 | Ledl | 351/242 |
| 4,285,580 A * | 8/1981 | Murr | 351/242 |
| 4,848,898 A * | 7/1989 | Massof | 351/242 |
| 6,210,006 B1 * | 4/2001 | Menozzi | 351/242 |
| 6,295,067 B1 * | 9/2001 | Dubnow | 345/419 |
| 6,547,737 B2 * | 4/2003 | Njemanze | 600/454 |
| 6,773,400 B2 * | 8/2004 | Njemanze | 600/454 |
| 7,059,719 B2 * | 6/2006 | Asher | 351/162 |
| 7,125,154 B2 * | 10/2006 | Blanc | 362/620 |
| 7,128,418 B2 * | 10/2006 | Sachtler | 351/242 |
| 7,133,209 B2 * | 11/2006 | Wursche et al. | 359/642 |
| 7,198,369 B2 * | 4/2007 | Chen et al. | 351/246 |

* cited by examiner

*Primary Examiner* — Francis Jaworski

(57) ABSTRACT

The present invention is a method for assessment of color processing mechanism in the human brain using cerebral blood flow velocity monitoring, specifically transcranial Doppler ultrasound. The method including steps of transluminating color discs from a light source of a specific color temperature, which act on the visual pathways and color centers to alter mean blood flow velocity in the cerebral arteries. The mean flow velocity is analyzed and using Fourier computation to calculate spectral density estimates. Opponent mechanism in the cortical and subcortical regions determined as opposing tendency for short wavelength versus medium wavelength or for medium wavelength versus long wavelength colors. The method is applied for diagnosis, and treatment of variety of conditions.

14 Claims, 32 Drawing Sheets

ACA

MCA

PCA

FRONT VIEW

BACK VIEW

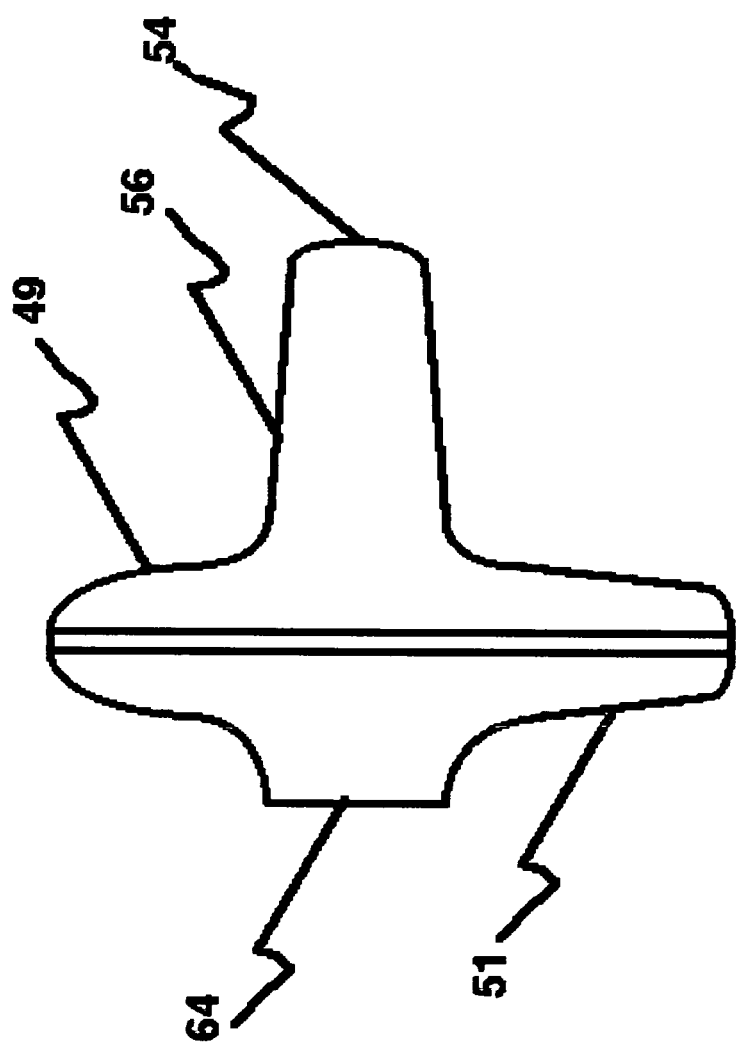
FIG. 8A LEFT SIDE VIEW

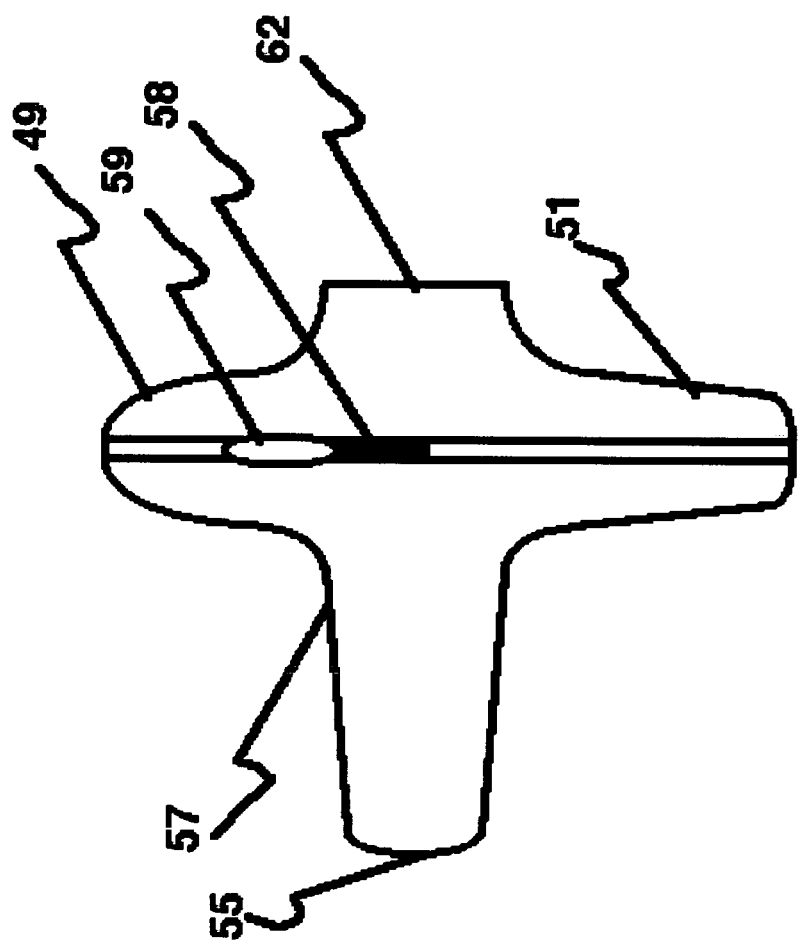

TOP VIEW

FRONT VIEW

SIDE VIEW

TOP VIEW

BOTTOM VIEW

METHOD FOR ASSESSMENT OF COLOR PROCESSING MECHANISM IN THE HUMAN BRAIN FOR DIAGNOSIS AND TREATMENT

STATEMENT REGARDING FEDERALLY SPONSORED RESEARCH OF DEVELOPMENT

Not Applicable

REFERENCE TO MICROFICHE APPENDIX

Not Applicable

BACKGROUND OF THE INVENTION

Color does not exist in the real world; it exists only in the perception of humans. Objects reflect many different wavelengths of light, which have no color. Color vision was developed as a way to tell the difference between the various wavelengths or light. Color processing involves two stages, first, the receptoral stage accomplished by three classes of cones, referred to as red, green, and blue, in the human retina. The receptors red, green and blue have peak absorption in the long (L$\lambda$=565 nm), medium (M$\lambda$=530 nm) and short (S$\lambda$=450 nm) wavelength ($\lambda$) of light, respectively. These cone receptors mediate color discrimination but do not code the perception of a single color. The cones are packed in the fovea region of the retina, where the center of visual field projects. In primates, two main types of retinal ganglions are distinguished, M and P. The P ganglion cells project to parvocellular (small) neurons and the M ganglion cells project to magnocellular (large) neurons in the lateral geniculate nucleus. Most P cells are color sensitive but M cells are not. The function of these three primary-color receptors in the eye and their neural connections, the P neurons, is to convey color information. In primates, optic nerve fibers from the left half of each retina (left visual field) project to the left lateral geniculate nucleus of the thalamus and fibers from the right half of each retina (right visual field) project to the right lateral geniculate nucleus. The crossing of the fibers takes place at the optic chiasm, the point at which the two optic nerves join. The fibers from the retinas to the chiasm are called optic nerves and those from the chiasm to the central nervous system are called optic tracts. The second stage of color processing is called the post-receptoral neural processing stage, where color opponency occurs. Color opponency refers to the capability of some neural cells to demonstrate chromatically and spatially opponent characteristics, which facilitate computation of simultaneous color contrast. De Valois described in a book titled "Spatial vision" published in New York by Oxford University Press, 1990, that many neurons in the visual thalamus, the lateral geniculate body, were opponent-process color-coding cells. The color-responsive P cells project via the lateral geniculate nucleus to the cortical blobs in the striate cortex area V1, and pre-striate area V4. Simultaneous color contrast suggests that, surrounding colors may influence perceived color as described by Albers J. in a hook titled "Interaction of color." published in New Haven, Conn. by Yale University Press, pages 20-21, 1963. It has been postulated that gamma-aminobutyric acid (GABA) modulates the color-opponent bipolar cells either through activating GABA receptors (GABA(A) and GABA(C)) on these cells directly or those on cone terminals indirectly, as described by Zhang D Q and Yang X L in an article titled "GABA modulates color-opponent bipolar cells in carp retina" published in Brain Research 1998, volume 792, pages 319-323. There is differential modulation by GABA of different postsynaptic mechanisms, respectively mediating signal transfer from R-cones and S-cones to the L-type horizontal cells. Furthermore, the dual action of GABA persisted in the dopamine-depleted retina, indicating no involvement of the dopaminergic interplexiform cells, as described by Xu H and Yang X in an article titled "GABA enhances short-wavelength-sensitive cone input and reduces red cone input to carp L-type horizontal cells," published in Brain Research Bulletin, 2000, volume 51, pages 493-497. This may suggest that neurons with the neurotransmitter GABA or GABAergic neurons mediate color opponent processing in the brain. In other words, a test of color opponent processing may provide a direct evidence of GABAergic function in the human brain. Another related phenomenon is color constancy, which refers to the ability to determine the color of an object independent of illumination conditions as described by Land E H and McCann J J in an article titled "Lightness and retinex theory." published in Journal of Optical Society of America 1971, volume 61, pages 1-11. Color constancy maybe mediated by "double opponent" cells as described by Daw N, in an article titled "Goldfish retina: organization for simultaneous color contrast," published in Science 1968, volume 158, pages 942-944; and by Livingstone M S, and Hubel D H in an article titled "Anatomy and physiology of a color system in the primate visual cortex," published in the Journal of Neuroscience 1984, volume 4, pages 309-356. Double opponency refers to the characteristics of a cell to respond to red and be inhibited by green in the center of its field but be excited by green and inhibited by red in the surround portion of the receptive field. Double opponent cells may act as "wavelength differencing system". The neurons in the blobs in V1 project to regions of area V2 termed "thin stripes" and from there to a color selective area identified as V4, as described by Zeki S in a hook titled "A vision of the brain, plate 16," published in Cambridge Mass. by Blackwell Scientific, in 1993. In the human brain, the color space includes a red versus green axis, a blue versus yellow axis, and in the luminance space, a white versus black axis as described by Conway B R in an article titled "Spatial structure of cone inputs to color cells in alert macaque primary visual cortex (V1)," published in the Journal of Neuroscience 2001, volume 21, pages 2768-2783; also described by Dacey D M and Lee B B in an article titled "The 'blue on' opponent pathway in primate retina originates from distinct bistratified ganglion cell type." published in Nature 1994, volume 367, pages 731-735. The cells of visual cortex have a columnar organization. Comparable regions of the retina project to the same region of the visual cortex. There are several visual areas (probably more than 32) in the human brain designated as V1, V2, V3, V4 and so on. Area V1 corresponds to original primary visual cortex mapped to the retina. The V1 provides input to V2, and V1 and V2 provide input to V3, and so on—that is, there is progressive funneling of visual information. The secondary visual areas respond equally well to input from both eyes. As both eyes focus on a near object, the image of the object falls over a slightly different region of the retinas of the two eyes. This retinal disparity, reflected in differing responses of the binocular cells of the secondary visual areas, is the major visual cue of three dimensions. Binocular interaction is another characteristic of the V1 area of the visual cortex. In the lateral geniculate nucleus every neuron receives their inputs from only one eye. The V1 neurons receive inputs from corresponding parts of the retina of both eyes. Binocular interaction does not occur at earlier levels due to stereopsis, the perception of depth, which relies on shifts in the position of the two eyes when focusing on objects at different distances. The latter is one clue the brain uses for depth perception. However, by creating a predominantly one visual field input of color stimulation during binocular view, the perception of depth by binocular interaction could be precluded. Since it would be inappropriate to mix the inputs from both eyes in a single neuron, before the information of color vision has been extracted as described by Regan D in a book titled "Spatial vision," published in London by Macmillan in 1991, pages 135-178. The projections from the retina to the visual cortex are highly organized. Neighboring regions of the retina make connections with neighboring geniculate cells. The left lateral geniculate nucleus has six layers that project to layer IV of the left visual cortex, and all six layers of the right lateral geniculate nucleus project to the right visual cortex. The inputs from the different layers of the lateral geniculate nucleus to the visual cortex are segregated so that a given cell in layer IV of the visual cortex receives input from one eye or the other but not from both. They cells of layer IV of the visual cortex are organized in columns in such a way that one column will respond to the left eye, an adjacent column will respond to the right eye. Moreover, cells receiving their only, or main input from one eye are also grouped together within the same area extending from the upper to lower cortical layers often referred to as an ocular dominance column. This characteristic is pronounced in the color selective area V4 which initially receives the input from the lateral geniculate nucleus. Two neighboring ocular dominance columns, representing both eyes each with its entire set of orientation columns, has been called a hypercolumn, as described by Gouras P in a book titled "The Perception of Colour volume 6—Vision and Dysfunction," published in England by Macmillan, in 1991, pages 179-197. Whereas the M cells of the retina project mainly to the posterior parietal cortex or dorsal stream for specialization in location of objects in space (where things are), the P cells project to inferotemporal cortex or ventral stream concerned with object vision (what things are). The secondary visual area V6 and visual-temporal area (TE) in the ventral stream respond to shape. The separation of M and P cells though not complete is important, since a thorough test of color perception should be concerned with identifying what things are by their colors but not by their shape or by location, in the post-receptoral stage, as well as discerning failure of receptoral input. These prerequisites for an ideal color test is not met by any existing color testing system in healthy subjects or in patients as would be evident in the brief review below.

Color vision abnormalities could occur at the first receptoral stage or second post-receptoral neural processing stage. At the receptor stage there are three types of color vision deficiencies: protanopia, deutanopia and tritanopia, corresponding to an absence or malfunctioning oblong, medium, and short wavelength-sensitive cone photoreceptors, respectively. The color defect called anomalous trichromacy is characterized by abnormal spectral absorption of the R receptor photopigment (protanomalous trichromat) or of the G receptor photopigment (deuteranomalous trichromat). Anomalous trichromat still require 3 primary colors in a mixture to perform color matching however, their ratio is abnormal compared to healthy subjects. Another form of color vision defects, called dichromacy, is characterized by an absence of the R receptor photopigment (protanope) or absence of the G receptor photopigment (deuteranope). Protanopes and deuteranopes require only two primary colors in a mixture to perform color matching. On the other hand, relative to the normal match, protanomalous trichromats add too much red to the mixture and deuteranomalous trichromats add too much green to the mixture. Protanopes match the red alone to the yellow, while deuteranopes match green only to the yellow, and any ratio of red to green in a mixture to yellow. Protanopes are insensitive to red light, that is, red light appears dimmer than yellow or green lights that look the same in brightness to normal observers. Deuteranopes have the same sensitivity to colors as normal subjects do.

Lesions of the post-receptoral stage of color processing are common in clinical practice. They implicate lesions of the visual pathways and impaired performance on color tasks in patients with hemispheric damage. Acquired color vision defects could commonly occur in patients with optic nerve disease such as retrobulbar optic neuritis caused by compression or toxic and demyelinating lesions as reviewed in detail by Griffin J F and Wray S H in an article titled "Acquired color vision defects in retrobulbar neuritis." published in the American Journal of Ophthalmology, 1978, volume 86, pages 193-201; and also by Linksz A, in an article titled "The clinical characteristics of acquired color defects," published in a hook edited by Staatsma B R, Hall M O, and Allen R A titled "The Retina, Morphology, Function and Clinical Characteristics." Berkley, University of California Press, 1969, pages 553-592. Lesions due to hemispheric damage have been described by De Renzi E and Spinnler H in an article titled "Impaired performance of color tasks in patients with hemispheric damage," published in the journal Cortex, 1967, volume 3 and pages 194-217. These include central dyschromatopsia, color agnosia, color aphasia and color amnesia. These pathologies are not well understood. Central dyschromatopsia is defined as impairment of color perception following a hemispheric lesion. Hemidyschromatopsia has been reported to follow hemianopia in the recovery stages from central optic pathway damage and to precede it in progressive disease. Some patients with apparently unilateral lesion may show contralateral hemianopia and ipsilateral dyschromatopsia. Patients with color agnosia but no dyschromatopsia, fail to name a color even though not aphasic or only mildly aphasic. The patient makes errors when asked to point to the color corresponding to a named object and, when presented with the drawing of an object colored incorrectly, shows a tendency to give the name of the typical color and not of the actual color, for example, a patient might say that a red colored leaf is green. Color aphasic patients make errors in naming or pointing to colors even though they do not have any perceptual defects and are not aphasic. Geschwind N and Fusillo M described in an article titled "Color-naming defects in association with alexia," in the journal Archives of Neurology, 1966, volume 15, pages 137-146, patients were said to have lesions of the left calcarine region (and hence produces right hemianopia) and the fibers of the splenium. As a consequence of the callosal damage, visual stimuli, received from the right calcarine region are prevented from reaching the speech area in the left hemisphere and a disconnection syndrome between visual perception and language occurs. This disconnection can be overcome in the case where the patient has to name objects, because the sight of object arouses somaesthetic associations in anterior parts of the right hemisphere, from which connections are available to the speech area over intact parts of the corpus callosum. By contrast, colors (and letters) do not arouse any somaesthetic association and thus cannot reach the speech area. Color amnesia is involved whenever the patient is required to recall the color of an object, whether by saying it or pointing to it taking into consideration interference from aphasia in the first case. Color amnesia is present when a patient uses wrong colors to paint common objects, for example using blue for cherries and strawberries instead of red.

Inherited color defect in the X chromosome occur in about 8% of men and 0.2% of women. Color defects could be used as marker genes for certain diseases such as bipolar disorders, which are also located on the X chromosome. Genes that have similar loci on a chromosome show linkage, that is, during cell division, chromosomes break and swap pieces, but genes that are close together still remain together. The color-blindness gene and the bipolar gene are linked. It has also been suggested that the bipolar-disorder gene is linked to Xga, the gene for another disorder called ocular albinism. The locus of the bipolar-disorder on the X chromosome appears to be between the Xga and the color-blindness genes. Chromosome marker studies are still recent and the use of color defects as markers has not been developed. Case studies may be used to illustrate these linkages, assuming that bipolar affective disorder can be inherited as a sex-linked recessive trait or as an autosomal recessive trait. This case inquiry involves two families: the Njokus and Ezes. Both families are afflicted with bipolar disorder as well as red-green color blindness. In the Njoku family 5 individuals suffer from both bipolar disorder and color blindness. If bipolar disorder and color blindness are both linked on the X chromosome as aforementioned, the mode of inheritance for these 5 individuals must be sex-linked recessive. It has also been observed that restriction fragment length polymorphisms (RFLP's) are associated with bipolar disorder, as well as linkage to chromosome 11 and to chromosome 18. Therefore further evidence of X-linkage would be the presence of RFLP's on the X chromosomes of these 5 individuals. Three individuals in the Njoku family are carriers of the disorder. They are the only ones who do not have the disorder but bear children who have the disorder. In the Eze family 3 individuals suffer from bipolar affective disorder. Four individuals have color blindness. The mode on inheritance in this family must be autosomal recessive. The evidence for this is that 3 out of four individuals with color blindness do not have bipolar disorder. Furthermore, all of the individuals with bipolar disorder show the presence of RFLP's on chromosome 11. Also one of the individuals in the family who does not have bipolar disorder possesses RFLP on chromosome 11 and has a child with bipolar disorder. If Njoku III2 marries Eze III8, a male child of theirs has a 27% chance of expressing bipolar affective disorder (since one parent has the disorder). Performing this type of tracing of inheritance patterns of bipolar affective disorder could be difficult, since some individuals who are carriers may not show any sign of the disorder. Also, some families with forms of the disorder may not have any of the genes thought to cause the disorder. The present problem is that bipolar disorder loci proposed are not specific enough to allow gene isolation and capture studies. A productive approach is to use some marker for screening large number of bipolar families and subjecting the data to genetic analysis using efficient evolutionary system coding.

Evolutionary systems contain large unstructured search spaces where no heuristics exists to guide the search. One way to reduce search time is to have the system learn more efficient problem specific coding containing minimal genotype size while at the same time not excluding potential solutions and producing small number of illegal solutions. To attain this type of precision, an evolutionary system identifies successful combinations of low-level (basic) genes and combines them into higher-level (complex) genes. Genes evolve in ever-lasting complexity, thus encoding a higher number of the original basic genes resulting in a continuous restructuring of the search space and allowing potential solutions to be identified in a shorter time. The present invention provides use of colors, which comprise several options (about 10 million separate colors are identifiable by the human eye) that could be matched to a network of genes presumably implicated in neuropsychiatric disorders. The latter may lead to identification of a variety of genes and their combinations in a network. It could be presumed that even when genes involved in perception of primary colors (red, blue and green) are normal, defects may arise in gene expression implicated in color mixing of the primary colors to secondary colors (for example yellow, magenta, cyan). In other words, the networking of genes controlling a behavioral trait known as epistasis, could be traced from the behavior implying a reverse epistasis to reveal abnormalities of gene network control. The potential for target stimulation of the brain to activate intrinsic genetic cascades mediated through several known systems for example, medium spiny neurons of the nucleus accumbens would find preventive and therapeutic applications for the present invention in medicine. This approach is hereby named spectrochromatographic prophylaxis and therapy. The latter implies that using the present invention, color wavelengths could be identified that have inhibitory effects for prevention of seizures and could be used to color spectacles or contact eye lens. In other conditions such as depression, both stimulatory and inhibitory effects of colors on blood flow would be useful and Once identified with the present invention could be used to color spectacles or contact eye lens. In other conditions such as acute or chronic pain therapy, selected wavelength of color using the present invention could be used to stimulate endogenous opioids in the brain to achieve anesthesia. A new approach for treatment of infectious and inflammatory diseases which is based on immunologic stimulation could be achieved with the present invention.

Both color opponent processing and anxiety neurosis may be linked. The benzodizepines (BDZ) specifically ease anxiety and panic attacks but are of little help in schizophrenia and may even make depression worse. The benzodiazipine receptors seem to exist together with the GABA receptor implicated in opponent color processing. The current concept suggests that activation of the BDZ receptor by a benzodiazepine acts via intermediary molecule to increase either the binding of GABA molecule to the GABA receptor or the coupling between GABA receptor and the chloride channel, or both as described in a book by Thompson R F titled "The Brain: a neuroscience primer", 3rd edition published in New York by Worth publishers pages 81-117, 2000. The link between color opponent responses and long-term psychostimulant abuse may be mediated by action of retinoic acid on H2 type horizontal cells. Following retinoic acid treatment, H2-type horizontal cells of dark-adapted retina became color-opponent and performed depolarizing responses to long-wavelength stimulation as described in an article by Pottek M and Weiler R titled "Light-adaptive effects of retinoic acid on receptive field properties of retinal horizontal cells", published in European Journal of Neuroscience, 2004, volume 12, Page 437. The signaling pathway using nuclear retinoic acid receptors has been implicated in medium spiny neuron gene expression in the ventral striatum as described in an article by McGinty J F in an article titled "Regulation of neurotransmitter interaction in the ventral striatum," published in a book by McGinty J F titled "Advancing from the ventral striatum to the extended amygdala," in the Annals of the New York Academy of Sciences, volume 877, pages 129-139, 1999. It is plausible that the effect of colors used in the present invention could change receptor sensitivity and tune off "cravings" in drug abuse. Furthermore, there is integration of postsynaptic glutamatergic, dopamine D1 and D2, and muscarinic receptor signals which trigger changes in gene expression in response to stimuli, such as drugs of abuse, which activate these systems. Stimulation of D1 dopamine receptors triggers the induction of immediate early genes (IEG) and the phosphorylation of cyclase response element binding protein (CREB) by activating multiple signal transduction cascades in medium spiny neurons. The latter cascades and the various neuronal networks that could be activated presumably using colors of specific wavelengths over the entire extended amygdala and ventral striatum to the hypothalamus-pituitary axis have applications in several medical, neurologic and neuropsychiatric conditions such as immune depression, hyperthyroidism, Cushing syndrome, diabetes, other endocrinological conditions, Parkinson's disease, epilepsy, depression, insomnia, schizophrenia, psychosis and others. It could be presumed that using the present invention selective wavelengths could be identified that produce desirable effects on psychostimulation that would find application of use in drug abuse rehabilitation and treatment. Depression is associated with cerebral hypoperfusion as described by Tiemeier H, Bakker S. L. M., Hofman A., Koudstaal P. J., Breteler M. M. B. in an article titled "Cerebral hemodynamics and depression in the elderly," published in the Journal of Neurology Neurosurgery and Psychiatry, volume 73, pages 34-39, in 2002. It would be desirable to have optical materials that could stimulate cerebral blood flow velocity to prefrontal cortex supplied by the MCAs in depression. Similarly, light passed through optical materials with appropriate wavelengths could act on suprachiasmatic nucleus and through interaction with the pineal gland and release of melatonin could have effect of sleep patterns.

The macular region of the "color centers" in the visual cortex V4 derive blood supply from both the calcarine branch of the posterior cerebral artery (PCA) and branches of the middle cerebral artery (MCA) as described by Till J S, in an article titled "Ophthalmologic aspects of cerebrovascular disease", in a book titled "Cerebrovascular Disorders" and edited by J F Toole, published by Raven Press in New York in 1984, pages 231-250. Furthermore, perfusion of most of the visual associative areas of the ventral stream derives supply from the MCA, while the primary visual area V1 is supplied by the PCA. Each of these major cerebral arteries of the circle of Willis comprising the anterior cerebral artery (ACA), the MCA and PCA, is divided into the cortical and ganglionic (subcortical) branches. The cortical branches of the PCA comprise the occipitotemporal arteries that supply the primary and some secondary visual regions, for example, the calcarine artery supplying the visual area V4 is mentioned above. The ganglionic branches comprise the thalamogeniculate arteries which supply the visual pathways of lateral geniculate nucleus. The MCA cortical branches comprising the anterior, middle and posterior temporal arteries supply the temporal lobe secondary visual areas as well as providing the calcarine branch that supplies the V4 area. The MCA gives the ganglionic branches that comprise the lenticulostriate arteries. It therefore follows that, by discerning blood flow to each specific region of the cortical and ganglionic branches of the visual pathways, processes at the second stage centers could be elucidated. Changes related to failure of receptoral input will be evident by the "fallout" of the effects of the related wavelength at cortical and subcortical sites.

The examination of color wavelength processing has been undertaken by Njemanze P C, Gomez C R and Horenstein S, in an article entitled "Cerebral lateralization and color perception: a transcranial Doppler study," published in a journal Cortex, 1992 volume 28, pages 69-75. The work by Njemanze et al (1992) showed that passive viewing of colors evoked mean blood flow velocity (MFV) changes using transcranial Doppler (TCD) technique. The TCD technique has been described in detail by Aaslid R in a book entitled "Transcranial Doppler Sonography" published in Wien by Springer Verlag, in 1986. In an article by Njemanze P C titled "Asymmetry of cerebral blood flow velocity response to color processing and hemodynamic changes during −6 degrees 24-hour head-down bed rest in men," published in Journal of Gravitational Physiology, 2005, volume 12 pages 33-41, it was demonstrated that light passed through Wratten color filters elicited MFV changes in the right MCA in men and showed opponent responses for blue versus yellow, and white versus black axes of color space. This opponent processing could be even further differentially characterized at subcortical and cortical areas using a new technique called functional transcranial Doppler spectroscopy (fTCDS). The fTCDS has been described in an article by Njemanze P C titled "Cerebral lateralization for facial processing: Gender-related cognitive styles determined using Fourier analysis of mean cerebral blood flow velocity in the middle cerebral arteries," published in the journal Laterality, 2007, volume 12, pages 31-49. fTCDS applies Fourier analysis to MFV data to discern changes related to visual processing at the cortical region and that at the subcortical region, offering opportunity to characterize the changes in the visual pathways from that at cortical processing centers.

Color defects are usually evaluated using 'book tests' such as the Ishihara pseudoisochromatic tests as described by Ishihara S in a manual titled "Tests for Colour-Blindness" published in Tokyo by Kanehara Shuppen, in 1971. There are 15 plates of the Ishihara test presented to each eye. Color vision is regarded as normal if 13 or more plates were read normally. Another test is the Farnsworth-Munsell 100 Hue test. The latter requires that the patient rearrange 85 randomly presented color chips in a regular color sequence as described by Farnsworth D in a manual titled "The Farnsworth-Munsell 100 Flue test for the examination of color discrimination.", published in Baltimore by Munsell Color Co., Inc., in 1957, pages 2-7. Acquired color defects are diagnosed based on tests of color matching using an apparatus called anomaloscope. The latter involves use of a bipartite field whereby, a spectrally pure yellow light in one half is matched to the other half with a mixture of red primary and green primary. Such an anomaloscope has been described in U.S. Pat. No. 3,947,099 to Grolman, U.S. Pat. No. 4,848,898 to Massa, and U.S. Pat. No. 6,210,006 to Menozzi. Other design modifications have been proposed, for example, U.S. Pat. No. 3,970,376 to Ledl describes a rotating disc or slides with pairs of test panels of different colors and transluminated by light source having a given color temperature to the subject tested. However, as with other prior art techniques, the examination relies on subject verbal feedback and some manual cooperation, which may be difficult to obtain in most patients with stroke or other neurological impairments by way of example. Given the verbal and manual cooperation, investigators have to obtain from subjects while using prior art, subjects require intact manipulospatial and language skills.

The examination by means of prior art, do not test all stages of color perception. In addition, the equipment is usually complex and not well adapted for patient use, challenging the patient with use of manipulospatial skills and higher order intelligence, which compound tests of just color vision. On the other hand the clinician requires special engineering skills to use the equipment with several man-hours lost in preparation and execution of tests. The results of the 'book tests' are highly complex to interpret and lack specificity of what exactly is tested and at which level of the color vision pathway could a lesion be uncovered. The prior art lacks specificity for testing and follow-up of patients with stroke lesions since the findings cannot pin-point the exact level of color vision where there is damage. The prior art is limited when it is necessary to examine color responses in brain rehabilitation process to uncover neuroplasticity, that is, ability to resume brain function after incapacitation. The prior art of anomaloscopes lack portability and by such, are not well adapted for use in space for astronauts in whom color perception could be used to examine adaptive behavioral processes. The prior art because of lack of specificity could not be applied to genetic analysis.

The problem of investigation of the color perception is solved by the system of the present invention. The solution is based on the neurophysiology of color processing in the human brain. Color information processed by opponent mechanisms implicating GABA neurotransmitters at the receptoral and neural phases activates primary visual area V1, V2, V3 and 'color specific' area V4 perfused by the PCA and MCA, with changes in the blood flow velocity in these arteries. The information channeled through cortico-subcortical pathways along the ventral stream enter the ventral striatum where they activate multiple signal transduction cascades in medium spiny neurons of nucleus accumbens, which in neuropsychiatric disorders cause abnormal opponent responses to short-wavelength versus medium- or long-wavelength. Opponent response is considered to be present when the differences in effects on MFV or its spectral density estimates for a pair of colors comprising short wavelength and the other medium or long-wavelength, is statistically significant or shows such a tendency. The invention consists of a method to provide a map of opponent mechanism at cortical and subcortical regions of each vascular territory of the circle of Willis. Such a map could be displayed as two joined squares or dominos for each color, showing accentuation state in shade (paved square) and attenuation state as unshaded area (unpaved square). One pair of domino could be used to represent two colors that display opponent mechanisms that is, activation or increased MFV as paved square but inhibition or decreased MFV as unpaved square. fTCDS permits even more detailed resolution, that is, using two sets of dominos side by side (tetramino) to show opponent mechanism for one pair of the colors at the cortical and subcortical regions, respectively. The map would show abnormalities of color opponent mechanism characteristic of a given neuropsychiatric condition. The information could be used in conjunction with clinical data to reveal genetic predisposition for such conditions as bipolar depression that may have genetic linkages to color vision defects. The map when used in conjunction with genetic analysis may reveal an efficient evolutionary system coding that could be applied to search for new genes. The present invention could be used to select colors that could cause inhibition of brain activity such as in photosensitive epilepsy and other types of seizures.

Prior art utilizes very expensive and complex electronics to produce colors and relics on subjective responses for evaluation. They are mainly comparative color tests using one color as fixed to compare to a variable color, rather than testing color processing opponent mechanism. Another obvious disadvantage is that complex electronics with even slight fluctuations in voltage would produce complex visual attributes of color such as hue, saturation, lightness (or value), brilliancy (or clearness), color efficiency (or vividness) that are discernable by the human visual system, resulting in inconsistencies. For example, U.S. Pat. No. 4,285,580 to Murr and U.S. Pat. No. 7,128,418 to Sachtler describe color vision testing apparatus that includes complex electronics such a cathode ray tube for producing the primary colors and microprocessor for photo-detection of signals. The prior art is imprecise in testing of color perception mechanisms and rather makes simplistic assumptions that color mixing could be impaired, and thus is designed to compare a fixed color hue to a variable color hue. The U.S. Pat. No. 3,653,771 to Piringer, U.S. Pat. No. 3,801,188 to Hunt, and U.S. Pat. No. 6,210,006 to Menozzi describes methods for conducting a color discrimination vision test that includes displaying a test object comprised of two separate fields wherein one field has a fixed color hue and the other field has a variable color hue.

SUMMARY OF INVENTION

These problems are solved by the system underlying the present invention in that two different devices one simple device for producing color and the other for examining the effects on the brain, are integrated into a system of devices. The invention permits a more precise examination of color vision by using a simple device to generate light of a specific wavelength and using a neuroimaging device to examine blood perfusion response to the color. The present invention uses a transcranial Doppler device to evaluate cerebral blood flow velocity changes associated with opponent color mechanism in the primary and secondary visual cortex areas perfused by the PCA and MCA. The discerning of opponent processing in the visual pathways and cortical centers is accomplished using a color device comprising a binocular apparatus for viewing of a color disc mounted on a reel and transluminated by light source of a specific color temperature.

In the present invention, the bandwidths of spectral emissions are generated when light of a constant color temperature passes through filters of specific wavelengths selected in such a way that color defects could be detected.

The present invention uses binocular view while excluding effects of binocular rivary, stereopsis and eye movements, by allowing the light path to pass from the left visual aperture while closing the right aperture to light.

The present invention allows assessment of the effects of colors on ocular dominance columns of the right visual field rather than effects on hypercolumns from both eyes.

The present invention permits precise examination of opponent response to wavelengths of light that comprise opponent pairs in the color space within a given vascular territory.

The present invention allows determination of selective receptoral failure for long, medium or short wavelengths by determining no increase in MFV compared to baseline dark condition.

The present invention allows determination of selective receptoral failure for long, medium or short wavelengths by loss of opponent response at cortical and subcortical regions using fTCDS.

The present invention determines abnormal hemispheric color processing by selective failure of opponent mechanism at the cortical but not subcortical region using fTCDS.

The present invention shows color opponent mechanisms within the subcortical and cortical regions of each vascular territory as paved and unpaved domino maps.

The present invention permits diagnosis of abnormal opponent mechanism in neuropsychiatric disorders. The present invention specifically incorporates information concerning normal or anomalous characteristics of the subject's color perception of a color set represented as paved and unpaved dominos of cortical and subcortical regional opponent responses combined into tetraminos for each vascular territory. Such tetraminos are used to represent a particular probability of genetic predisposition to a neuropsychiatric disorder such as major depression, bipolar depression, schizophrenia, anxiety neurosis, and drug abuse. Depending on the normal and anomalous variants for the different color sets the corresponding controlling genes could be identified.

The present invention permits diagnosis of abnormal opponent mechanism associated with neuroplasticity during psychophysiologic adaptation to special environments such as in microgravity, hypergravity, high altitudes, deep sea diving, and hyperbaric conditions.

BRIEF DESCRIPTION OF SEVERAL VIEWS OF THE DRAWINGS

FIG. 8A shows the left side view of the color device of the present invention.

FIG. 8B shows the right side view of the color device of the present invention.

DETAILED DESCRIPTION OF THE INVENTION

Figure 1A:
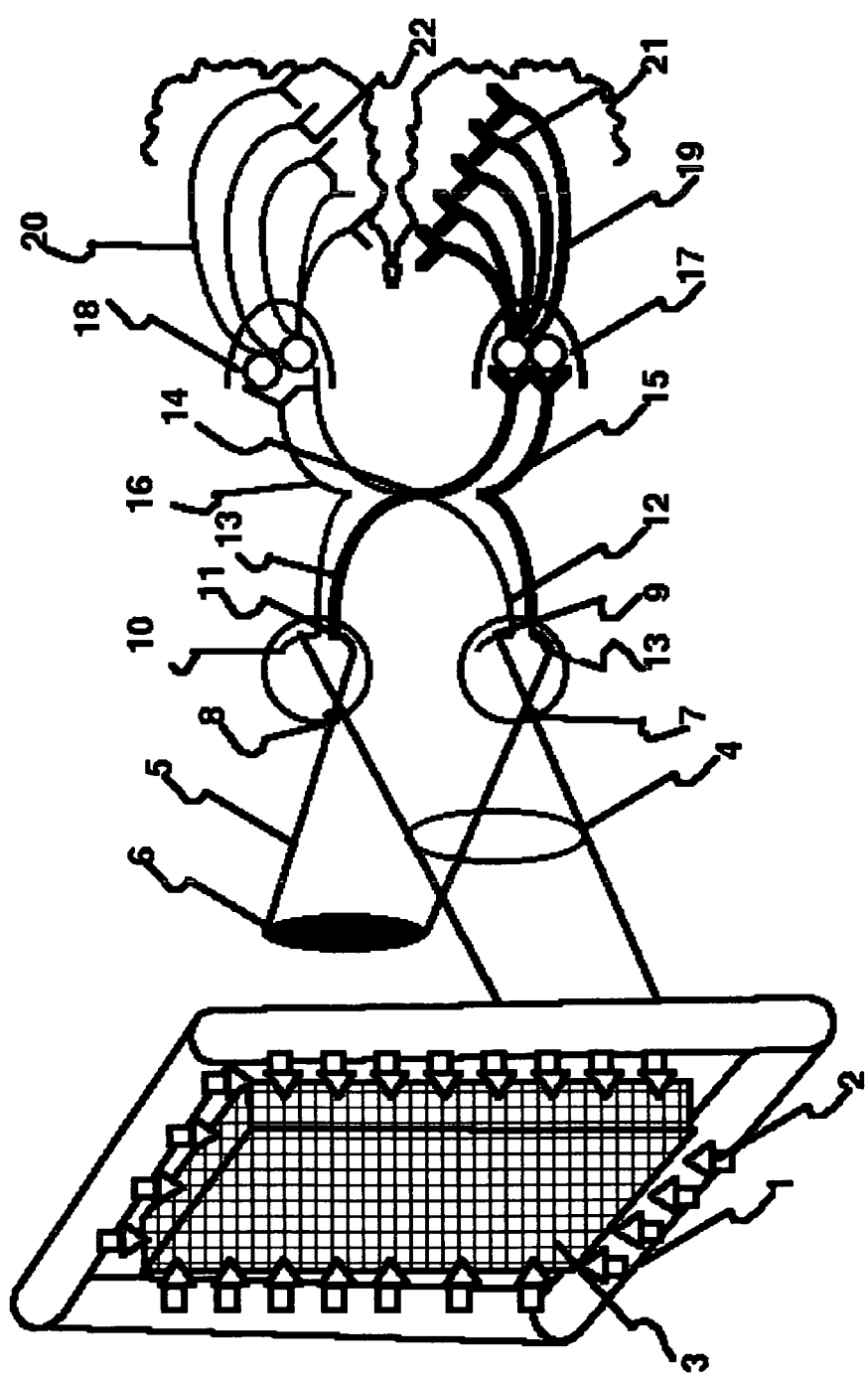
FIG. 1A shows the schematic diagram of the present invention and the neurophysiological basis.
Figure 1B:
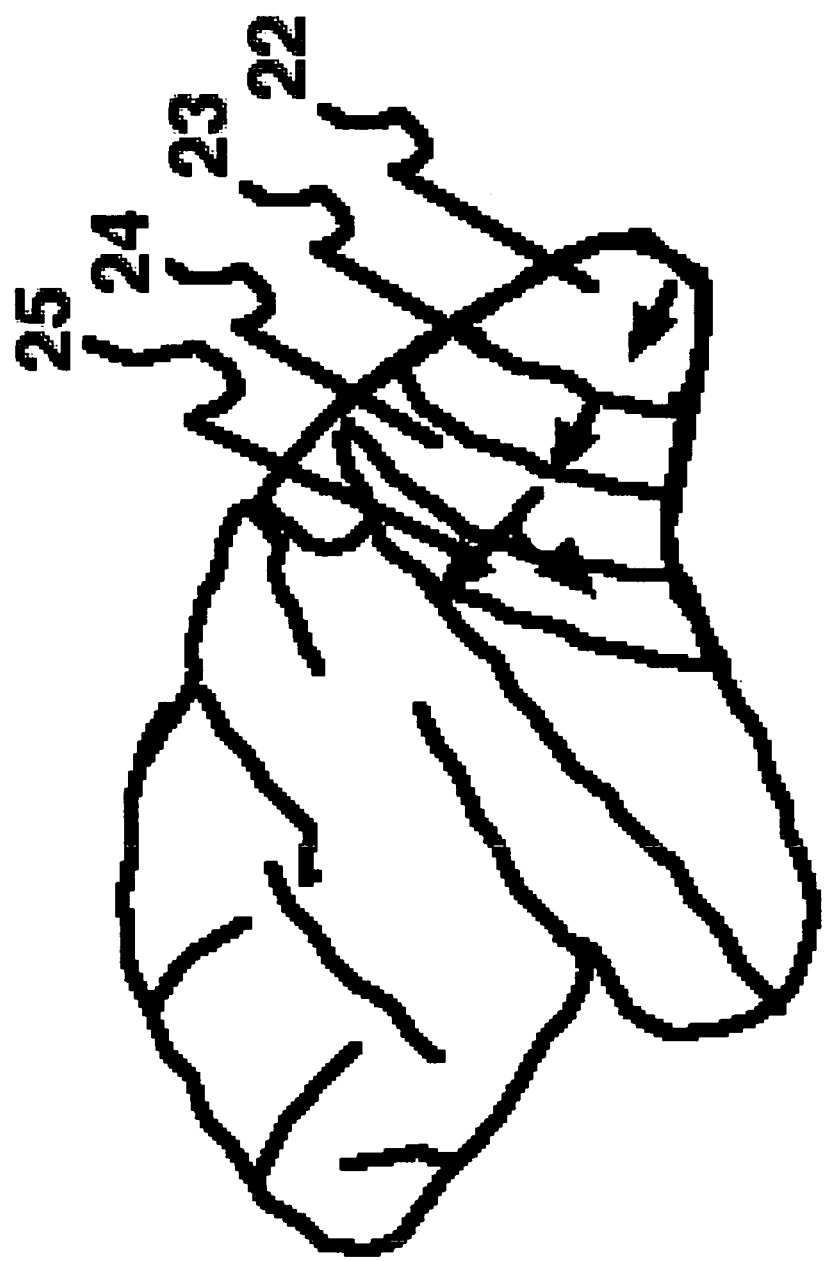
FIG. 1B shows the primary and secondary visual areas.

The schematic diagram of the present invention and the neurophysiological basis are illustrated in FIGS. 1A and 1B. As shown in FIG. 1A therein, a light source 1 of constant color temperature (a measure which defines the color of a light source relative to the visual appearance of the light radiated by a theoretically perfect radiator, or blackbody, heated to incandescence and is expressed in Kelvin (K)) is used to produce day light of 6504K 2 from cold cathode fluorescent tubes along the four sides by way of example. The backlighting, is fitted with a light guide 3 such as described in U.S. Pat. No. 7,125,154 B2 to Blanc such that the lighting is homogenous. The light path passes into the right visual field 4 but not left 5, because the latter is blocked with a dark slide 6. The light rays passes through the left eye lens 7 and right eye lens 8 to fall on the right half of the left eye retina 9 and right eye retina 10, but not the left half 11. The cone photoreceptors in the right half of the retina connect the color coding neurons, the P neurons, and send information through the optic nerve fibers from the right half 12 but not left half 13. Two third of the fibers cross to the contralateral side at the optic chiasma 14, and together with one third of the uncrossed fibers from the left half and right half they comprise the left 15 and right 16 optic tracts that reach the left 17 and right 18 lateral geniculate nucleus, respectively. It is intended that the P neurons of the right lateral geniculate nucleus 18 would be stimulated but not left 17, so that the left lateral geniculate nucleus 17 does not convey color information through the left optic radiation 19, while the right optic radiation 20 carries color information. As a consequence, the left color centers 21 would not be stimulated while the right color centers 22 would show opponent color processing mechanism. As shown in FIG. 1B, color processing would pass through the ventral stream from V1 22 to V2 23, from V2 to V3 24, from V3 to V4 25 and so on.

Figure 2:
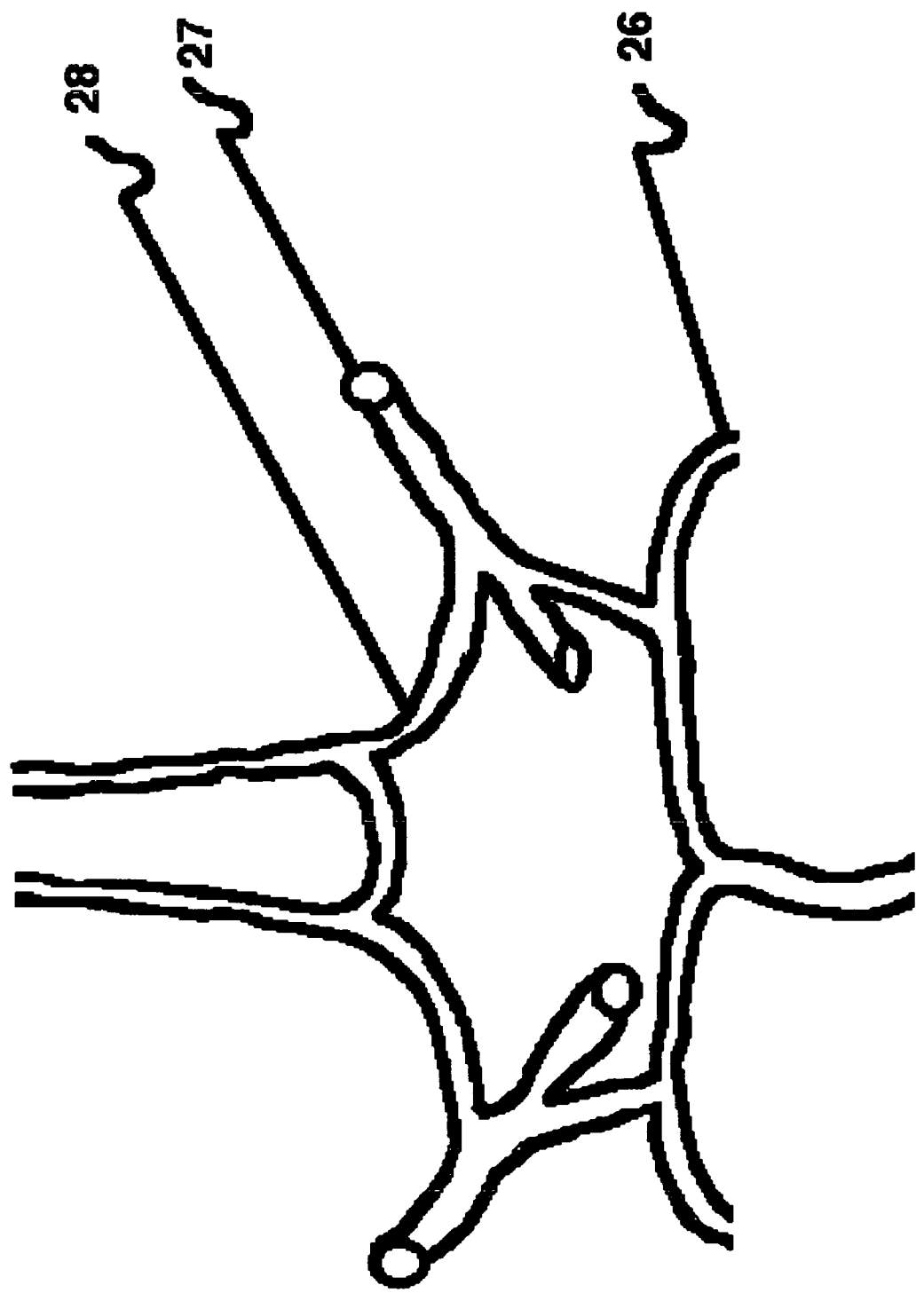
FIG. 2 shows the arteries of the circle of Willis within which blood flow velocity changes are monitored with the present invention.

As shown in FIG. 2 ventral stream particularly the macular region perfused by the calcarine branches of the PCA 26 and MCA 27 would be expected to show changes in mean blood flow velocity with opponent color processing rather than ACA 28.

Figure 3A:
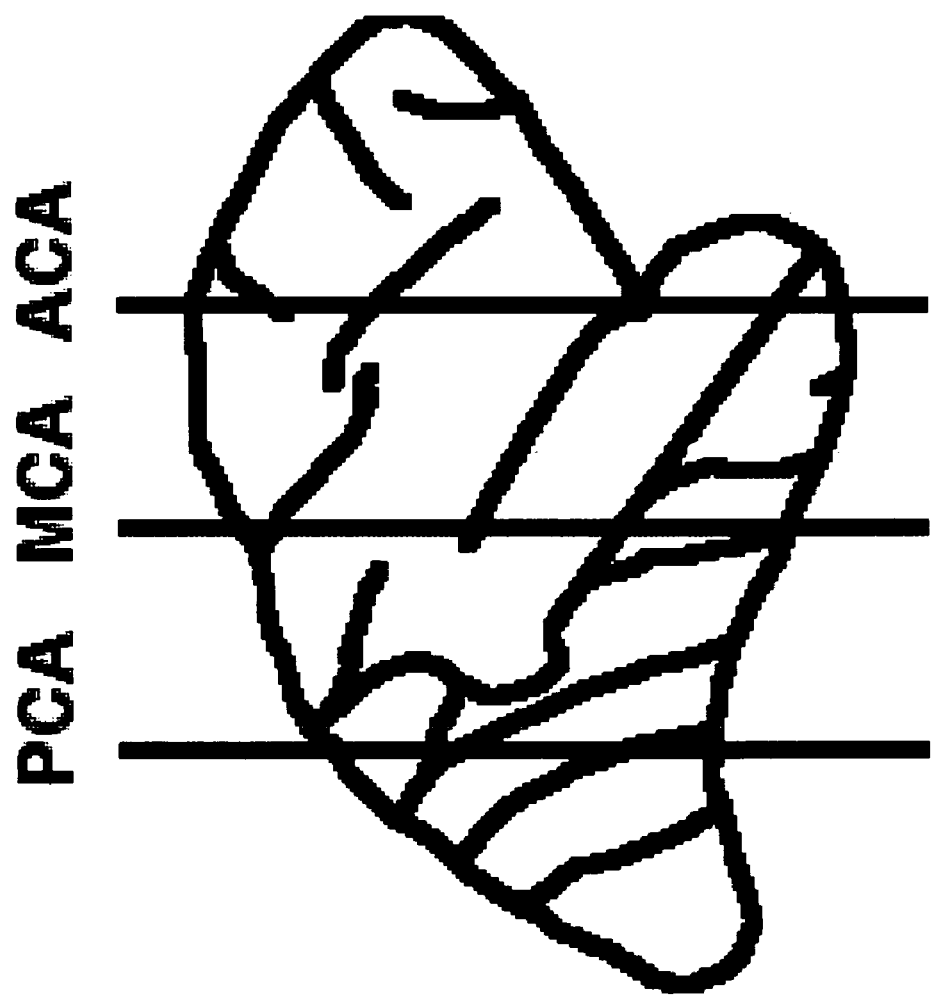
FIG. 3A shows the cross-sections of the brain vascular territories where blood flow velocity could be monitored with the present invention.
Figure 3B:
FIG. 3B shows the vascular territory of the ACA with cortical and subcortical arterial branches.
Figure 3C:
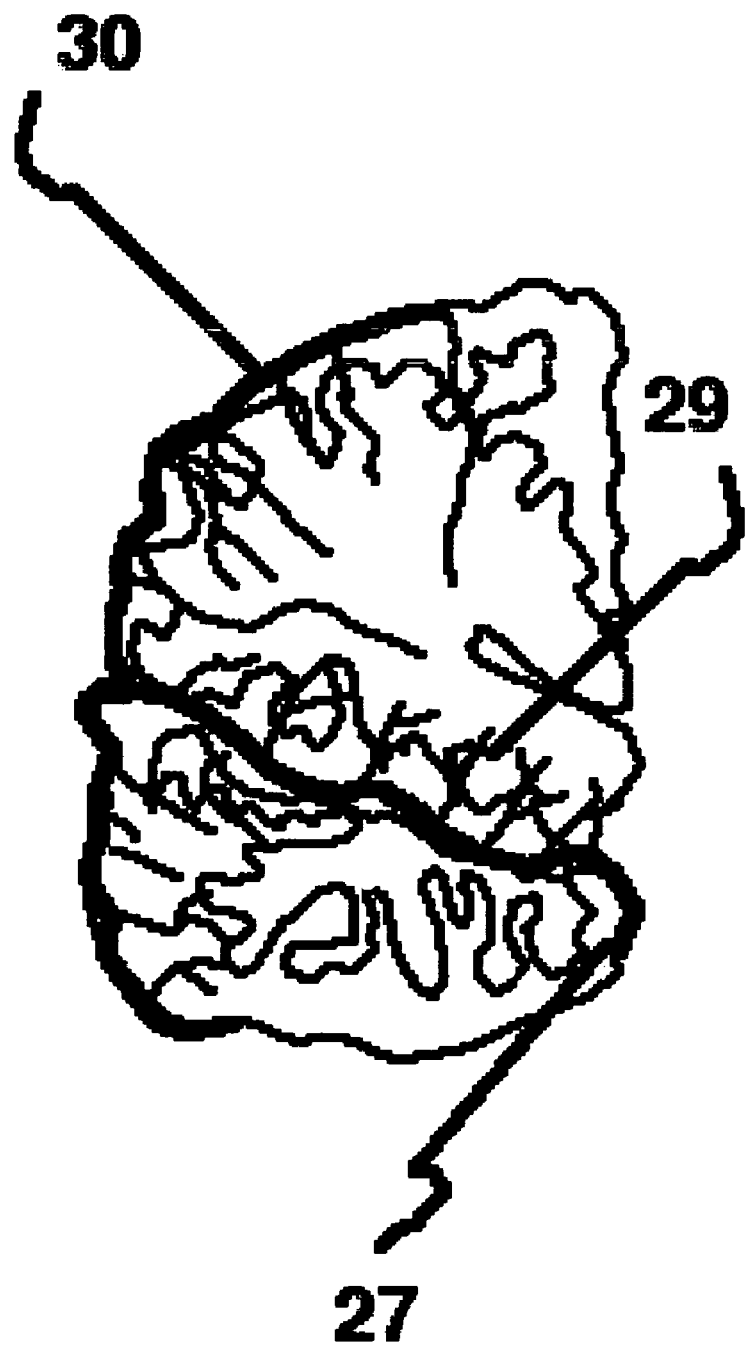
FIG. 3C shows the vascular territory of the MCA with cortical and subcortical arterial branches.
Figure 3D:
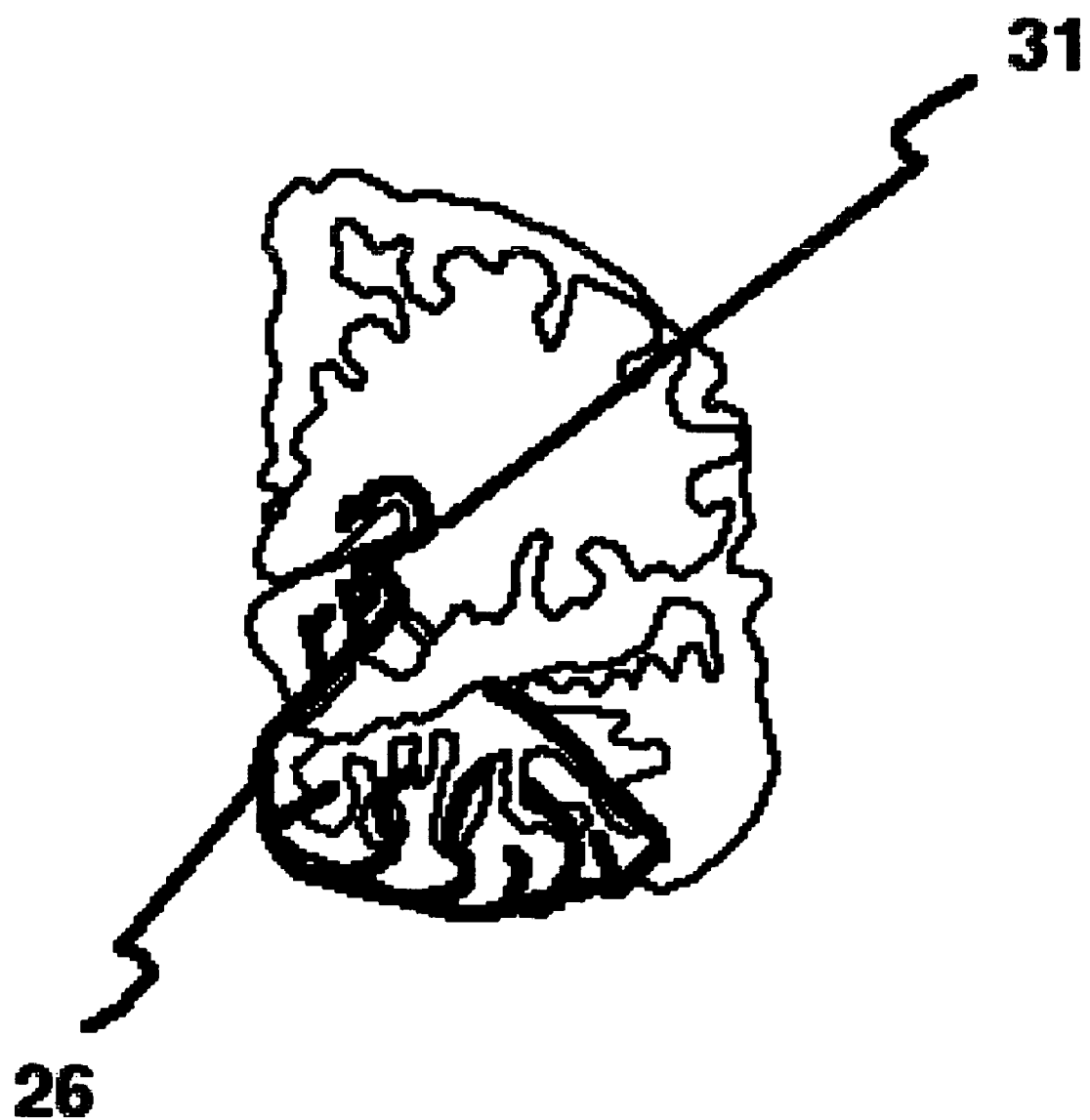
FIG. 3D shows the vascular territory of the PCA with cortical and subcortical arterial branches.

As shown therein in FIG. 3A, a cross-section of the vascular territories of the PCA, MCA and ACA reveal that the ACA 28 would be more implicated in changes within the dorsal stream as shown in FIG. 3B. FIG. 3C shows that the secondary visual areas of the ventral stream are supplied by the ganglionic (subcortical) 29 and cortical 30 branches of the MCA 27. FIG. 3D shows that the PCA 26 supply the primary visual cortex and visual pathways 31 via the calcarine and subcortical branches. Therefore monitoring of mean blood flow velocity in the MCA or PCA during color stimulation using the present invention would reveal opponent color processing.

Figure 4A:
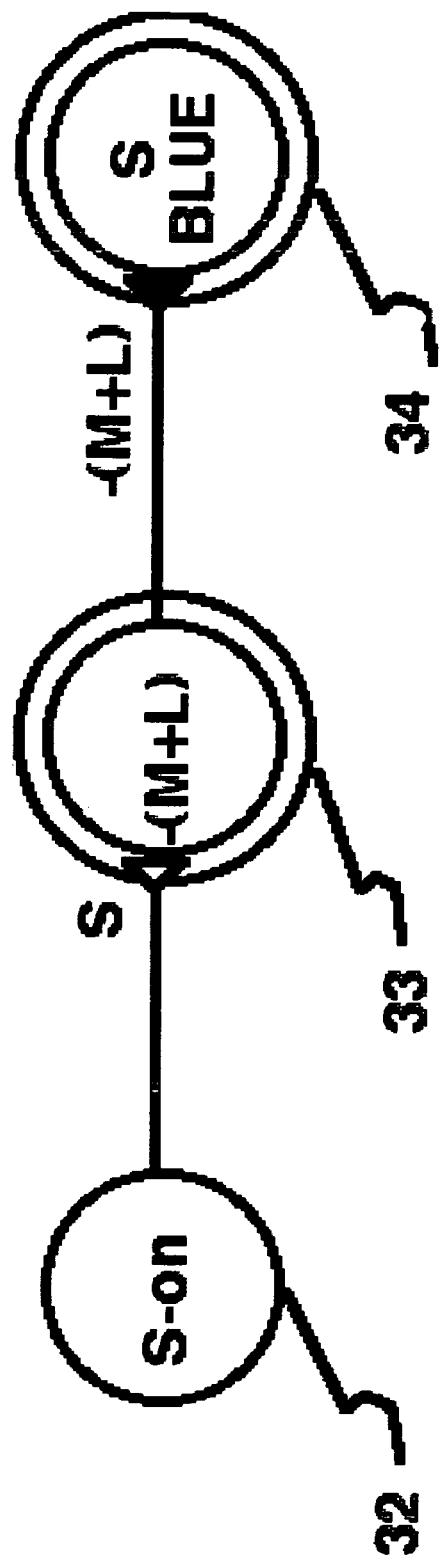
FIG. 4A shows the logical synaptic arrangement at receptoral and neural stages that lead to the construction of chromatic contrast detectors that sense blue-yellow contrasts with use of the present invention.
Figure 4B:
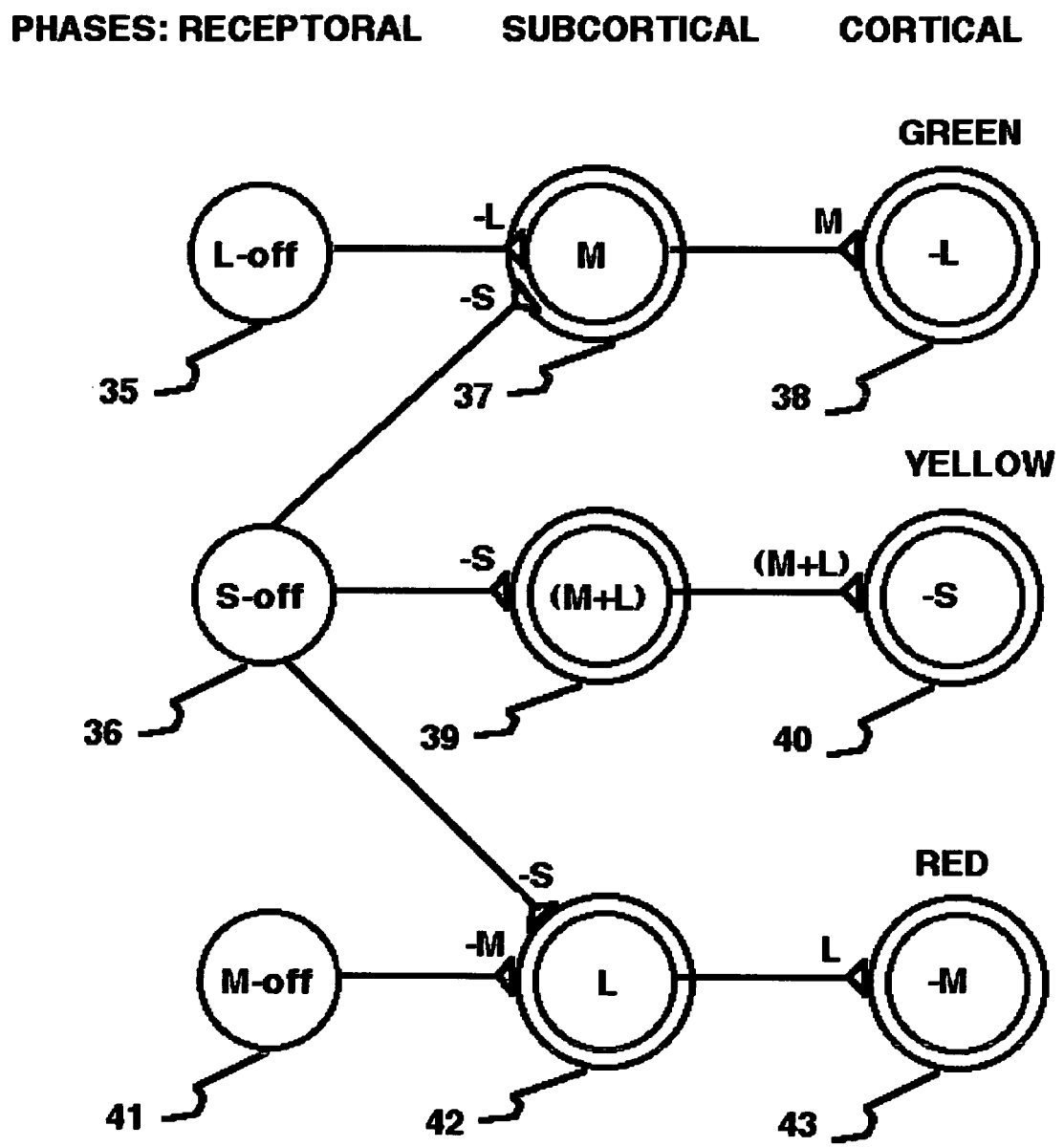
FIG. 4B shows the logical synaptic arrangement at receptoral and neural stages that sense green, yellow and red with use of the present invention.

The invention presumes that there are two types of neural networks implicated in color processing: one for short-wave (S neurons) and the other for medium (M-neurons) and long wave (L-neurons). The M- and L-neurons are spatially co-localized. FIG. 4A shows the logical synaptic arrangement at receptoral and neural stages that lead to the construction of chromatic contrast detectors that sense blue-yellow contrasts with use of the present invention. Retinal receptors that respond to blue (S-on receptor) 32, activate synaptic terminals (open triangle) of S-neurons resulting in S surround at subcortical region but −(M+L) at the center 33. The (M+L) cells at their synaptic terminals at the cortical region would be inhibited (closed triangle) resulting in −(M+L) surround and S center or blue-yellow contrast 34. FIG. 4B shows that retinal receptors that respond to disappearance of red (L-off) 35 would also respond to disappearance of blue (S-off) 36 and thus would inhibit the M-neurons and S-neurons resulting in (−L) and (−S) surround at the subcortical region leaving only the M-neurons excited 37, which in turn send synaptic terminals at the cortical region with M surround and center or green-red contrast 38. The retinal receptors that are sensitive to disappearance of blue (S-off) could be excited alone and their synaptic terminals would inhibit S-neurons resulting in −S surround, and the central (M+L)-neurons at the subcortical region 39, send synaptic terminals to the cortical region creating (M+L) surround and −S center or yellow-blue contrast 40. Some retinal receptors are sensitive to disappearance of green (M-off) 41 as well as blue (S-off) 36 and thus result in −M and −S surround leaving L center at the subcortical region 42. The synaptic terminals of the center L-neurons at the cortical region create an L surround leaving predominantly −M center or red-green contrast 43. The present scheme implies that simultaneous color contrast as a neural mechanism does not occur in the retina or lateral geniculate nucleus but in the visual cortex. It occurs by means of synaptic connections linking subcortical and cortical centers of a given chromatic space.

Figure 5:
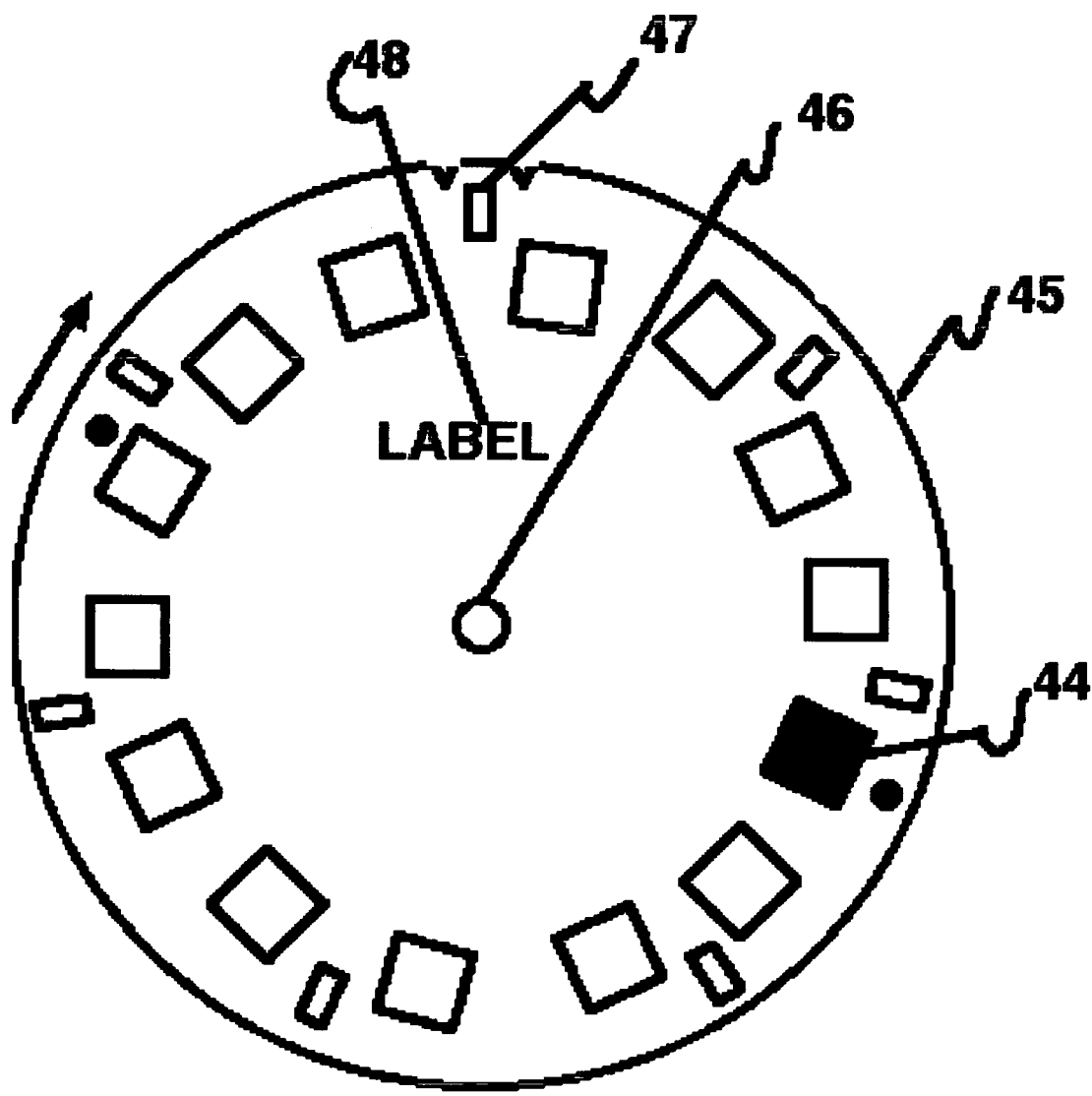
FIG. 5 shows the fourteen color and dark slides on the reel used with the present invention.

FIG. 5 shows the fourteen color and dark slides on the reel used with the present invention. The method to produce this disc is similar to that described in U.S. Pat. No. 6,295,067 B1 to Dubnow. The slides 44 are fitted onto a circular disc 45, which anchors at central hole 46 for rotation, and uses rectangular perforations 47 as anchor to move the slides into position. The slides 44 may comprise optical materials of known dominant wavelength (hue), excitation purity (saturation) and percent luminous transmittance (brightness). Optical materials such as Wratten filters (Eastman Kodak) could be used. In other cases the present invention could be applied to choose appropriate molding composition for optical materials produced as described in U.S. Pat. No. 7,133,209 to Wursche, or materials used for production of color contact lens by Bragg diffraction as described in U.S. Pat. No. 7,059,719 to Asher and other methods. Each rotating circular disc 45 is fitted with a slide 44 that meets the intended purpose of the investigator. The slide 44 in position is labeled 48 and choice of the material that produces the desirable effects on blood flow velocity could be made appropriately. A set of slides on a disc could be intended to select wavelengths of light that stimulate endogenous opioids in the brain to prevent pain, and another set to induce release of inhibitory neurotransmitters that will prevent seizures and yet another set of discs could be used to select wavelengths of light which induce release of neurotransmitters that may cause reduction in the mean flow velocity in the right MCA but not left MCA in patients with depression. Thereafter, the spectrophotometric curves and the stability of the optical materials are determined for further use in manufacturing of spectacles or contact lenses for such applications.

Figure 6:
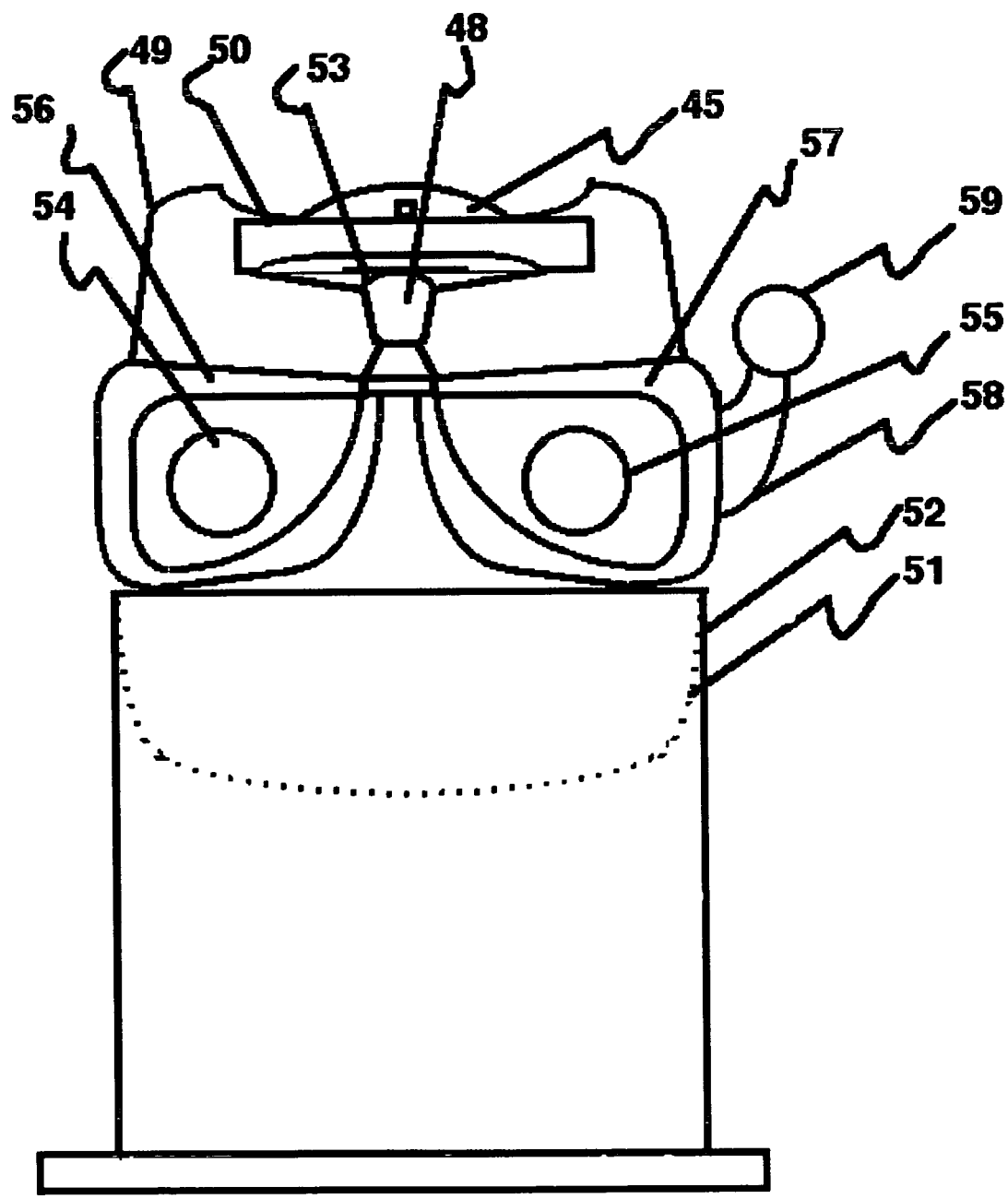
FIG. 6 shows the front view of the color device in one embodiment of the present invention.

FIG. 6 shows the front view of the color device of the present invention. The device 49 outer and inner surfaces could be painted black as a means to prevent extraneous color effects. The rotating circular disc 45 is inserted through a slit opening 50 at the top and push down to the bottom part 51 of a hand-held version, or upper part of a stand in the stationary version 52. The inserted disc slide label 48 could be viewed from a fenestration 53 at the front part of the device. The left eye piece 54 and right eye piece 55 allow view of light passing from the slide through a left 56 and right 57 light paths of the left and right visual fields, respectively. The slide positions could be mechanically changed using a lever 58 and holder 59 in one version of the device or automatically using a switching device in another embodiment of the present invention.

Figure 7:
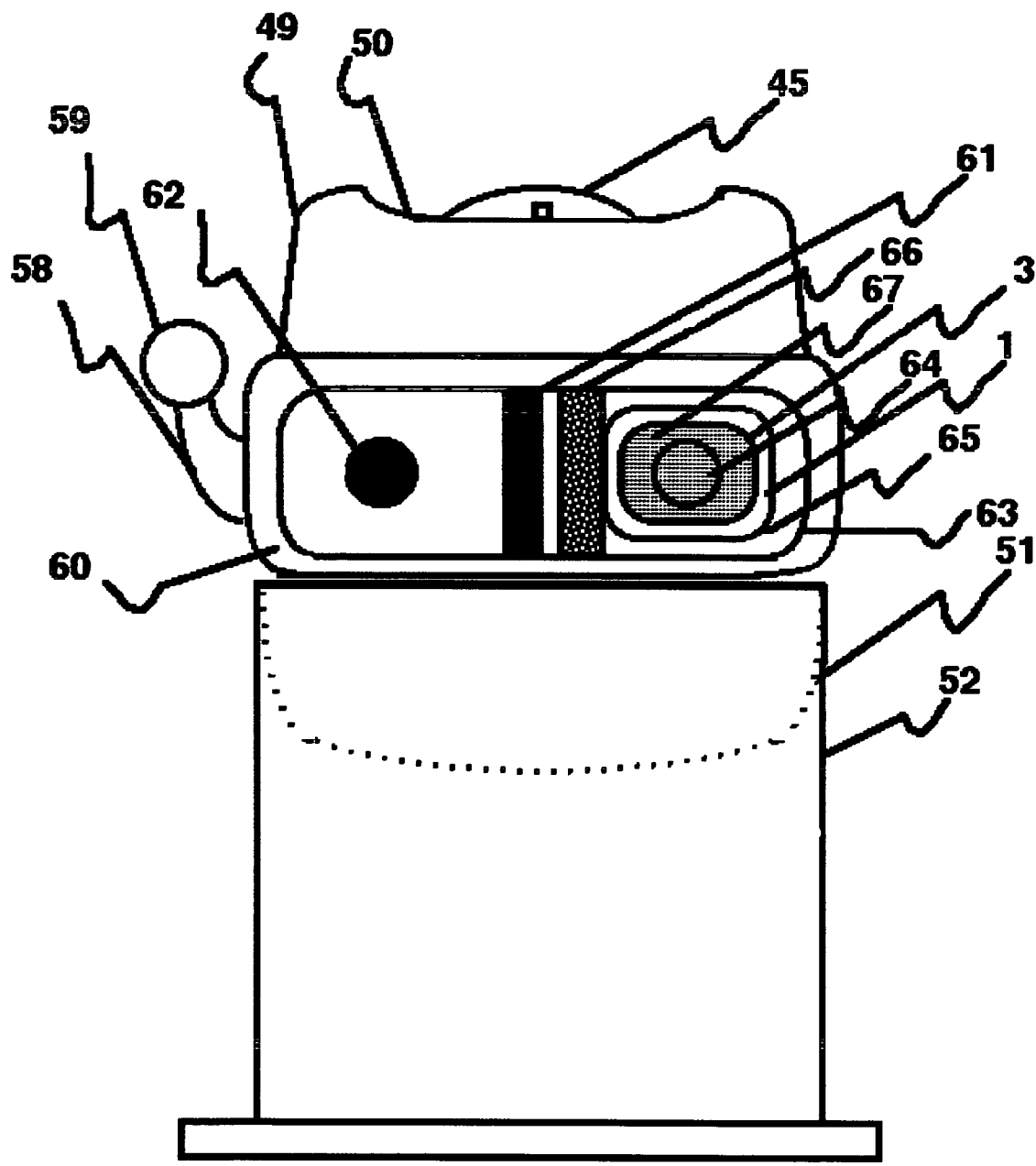
FIG. 7 shows the back view of the color device in one embodiment of the present invention.

FIG. 7 shows the back view of the color device of the present invention. The hack optical side 60 is divided by a bridge 61 into the dark right half that covers the aperture with a dark slide 62 and the light reflection left side 63 that allows light through the transparent left aperture 64. Light from a four sided fluorescent lamp 1 is fitted into a four-corner rim space 65 with the supporting electrical circuit 66 placed in the midline portion. The rectangular space within the fluorescent lamp 1 is fitted with a light guide 3 to cover the entire space 67 surrounding the light left aperture 64.

FIG. 8A shows the left side view of the color device of the present invention. The light from the left aperture 64 passes through the path 56 to the left eye piece 54. On the other hand, as shown in FIG. 8B, the right side view of the color device of the present invention, no light passes directly through the right aperture 62 through the pathway 57 to the right eye piece 55. As a result, the left visual field 5 (FIG. 1A) is dark, while there is light in the right visual field 4 (FIG. 1A).

Figure 9A:
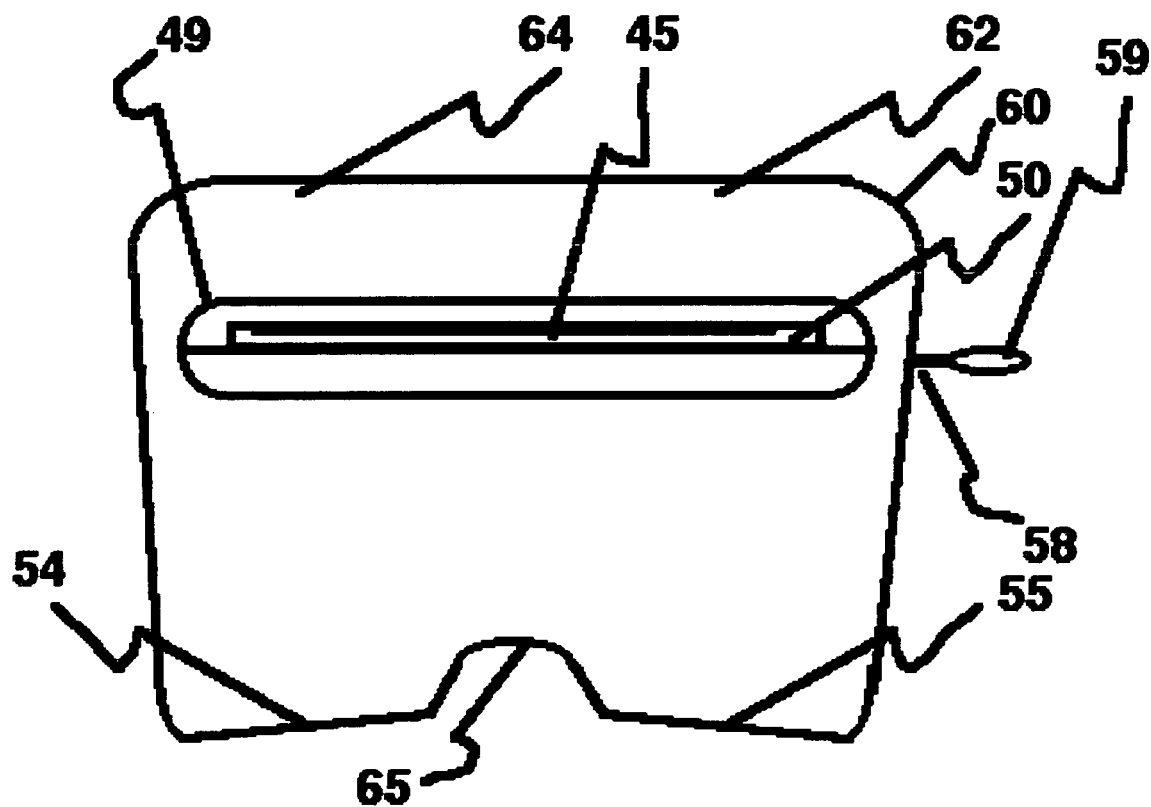
FIG. 9A shows the top view of the color device of the present invention.
Figure 9B:
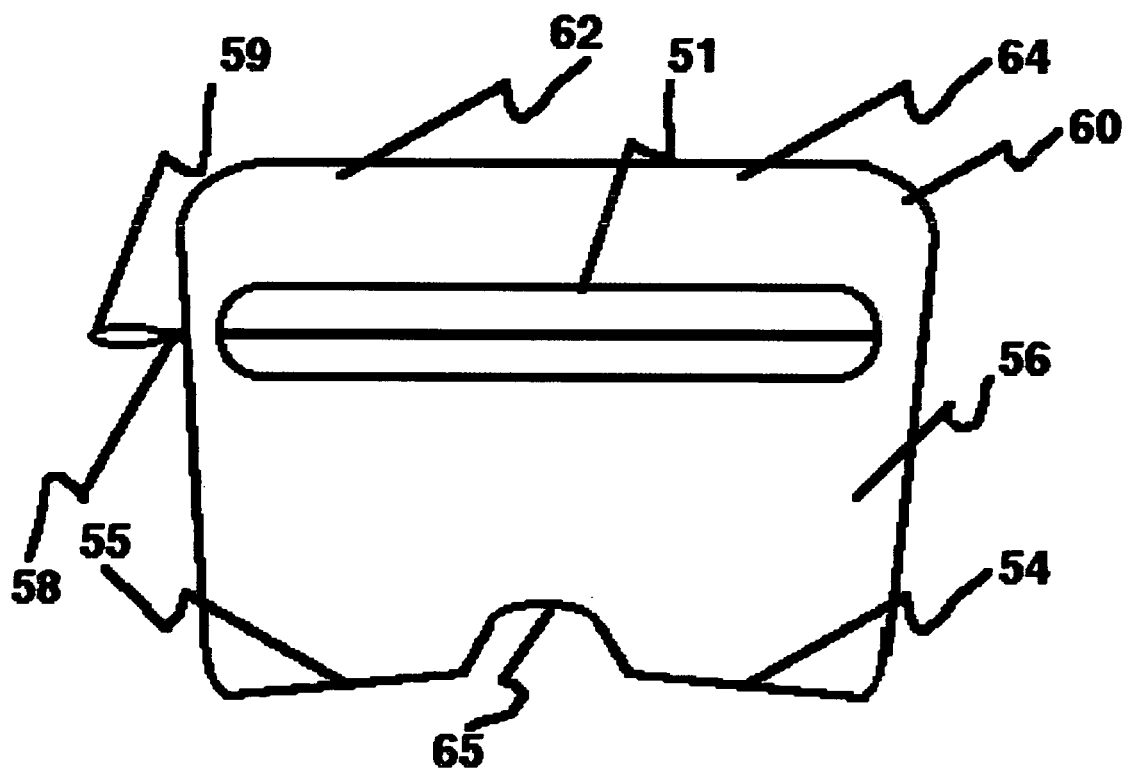
FIG. 9B shows the bottom view of the color device of the present invention.

FIG. 9A shows the top view of the color device of the present invention. A space 65 is provided for the nose ridge to permit firm fitting of the device on the face. This view allows visualization of how the disc 45 fits into the center of the slit opening 50 at the top. FIG. 9B shows the bottom view of the color device of the present invention.

Figure 10A:
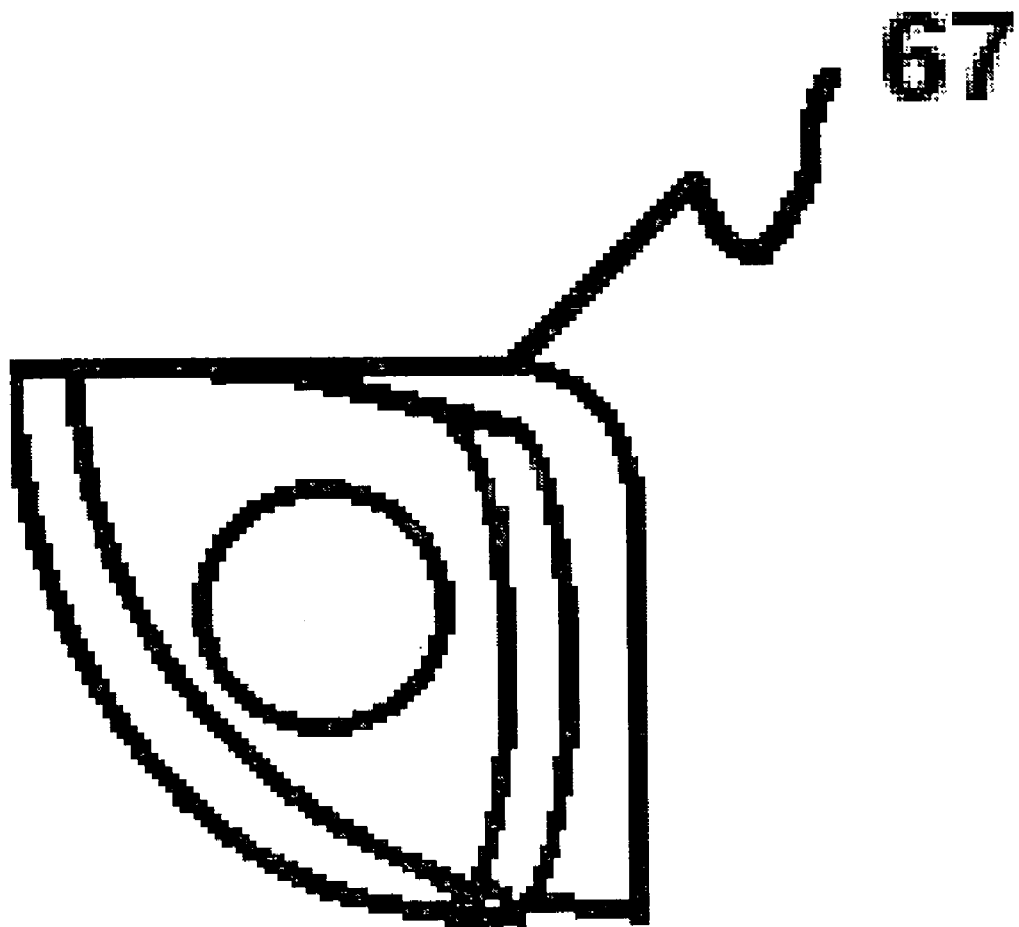
FIG. 10A shows the front view of the right eyepiece rubber flap of the present invention.
Figure 10:
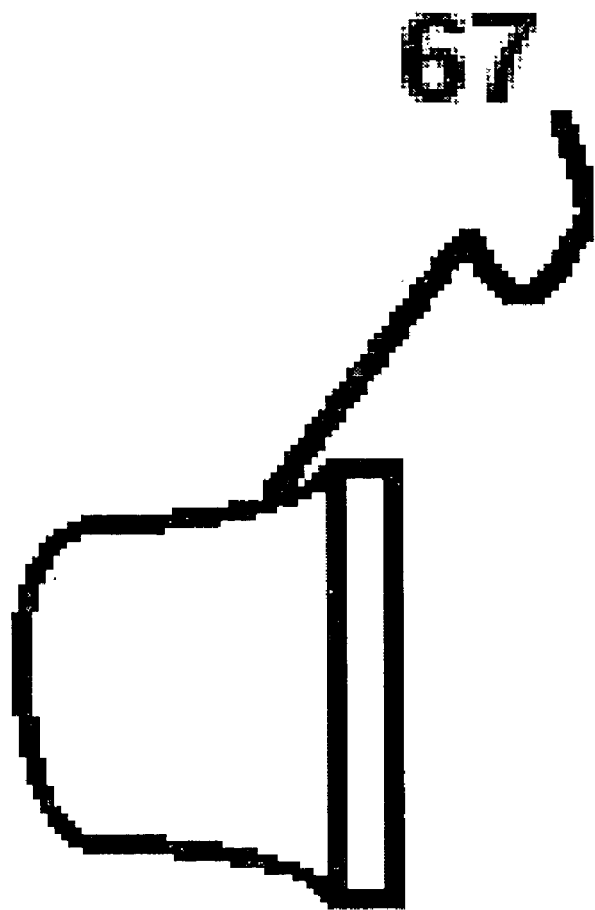
FIG. 10B shows the side view of the right eyepiece rubber flap of the present invention.
FIG. 10C shows the top view of the right eyepiece rubber flap of the present invention.
FIG. 10D shows the bottom view with fitted eyepiece rubber flaps of the present invention.
Figure 10:
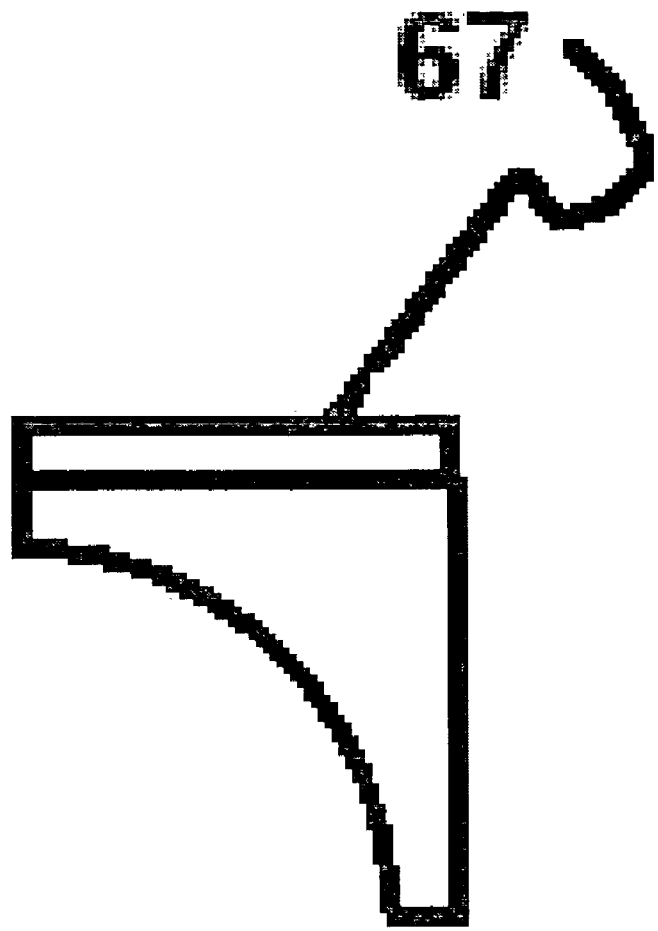
Figure 10:
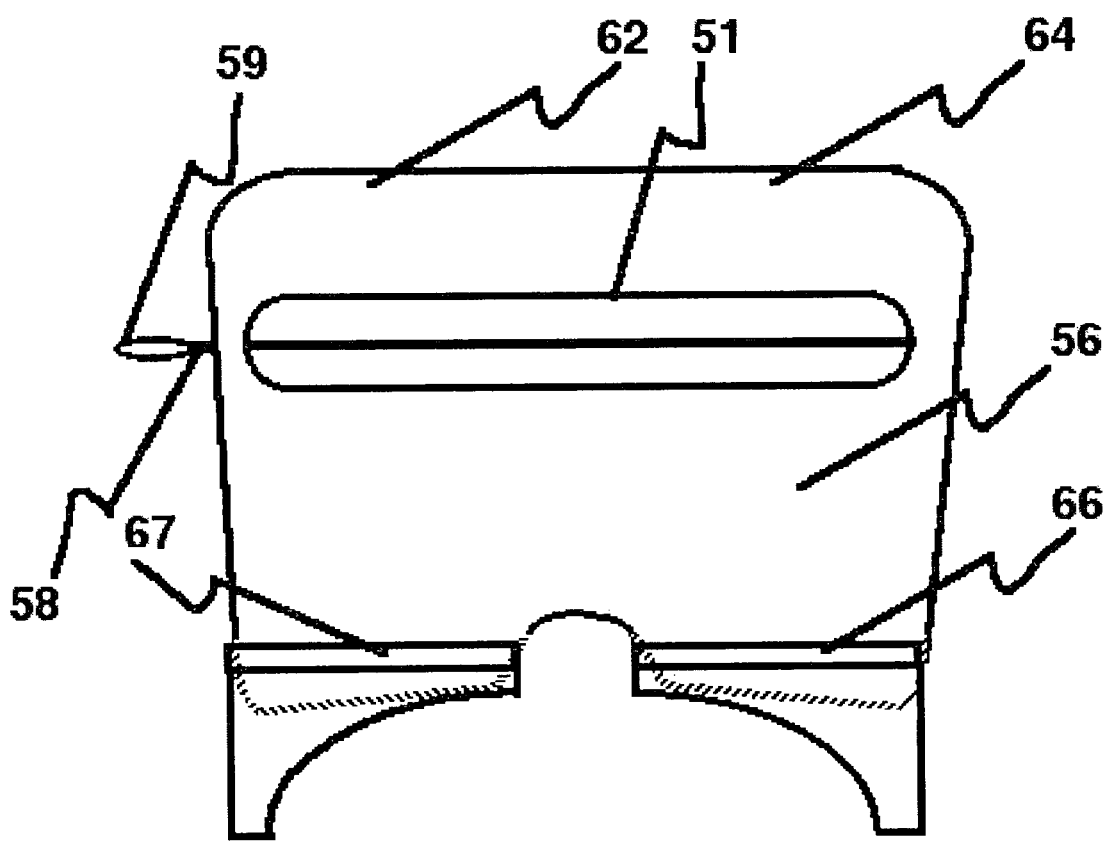

FIG. 10A shows the front view of the right eyepiece flap of the present invention when fitted with a soft rubber flap 67 to exclude ambient light. FIG. 10B shows the side view of the rubber flap 67. FIG. 10C shows the top view of the rubber flap 67. FIG. 10D shows the bottom view of the color device when fitted with both left 66 and right 67 rubber flaps.

Figure 11:
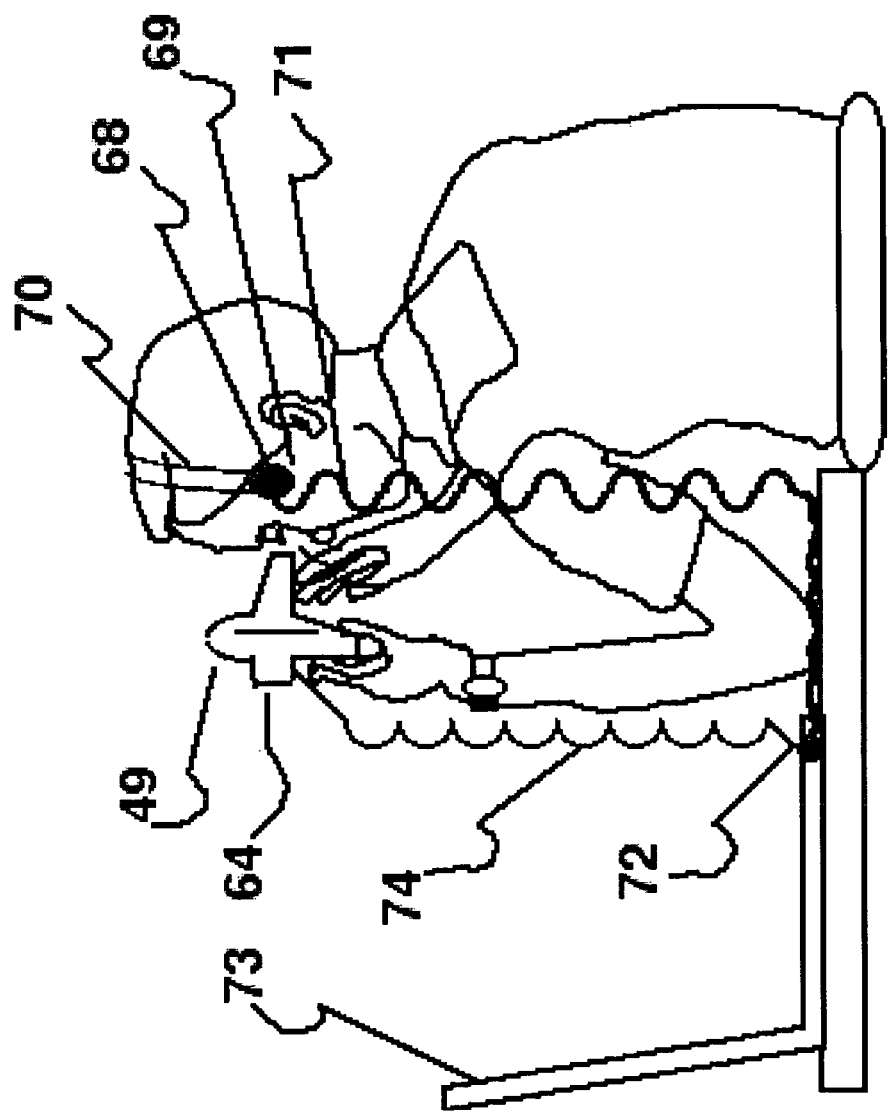
FIG. 11A shows the whole embodiment of the handheld version of the color device and the blood flow velocity monitoring device of the present invention used for a subject in sitting position.
FIG. 11B shows the whole embodiment of the hands-free version of the color device and the blood flow velocity monitoring device of the present invention used for a subject in sitting position.
FIG. 11C shows the whole embodiment of the handheld version of the color device and the blood flow velocity monitoring device of the present invention used for a subject in lying position.
Figure 11:
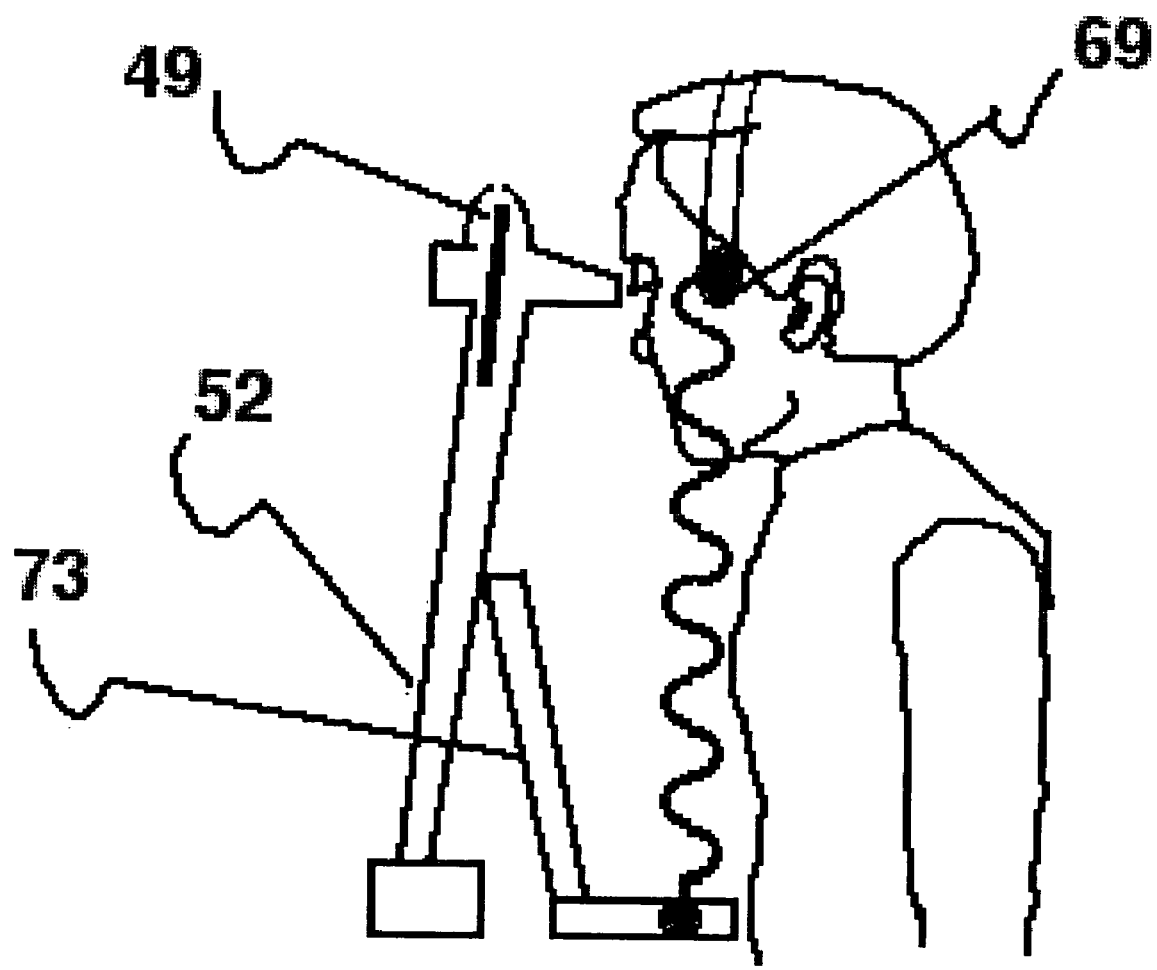
Figure 11:
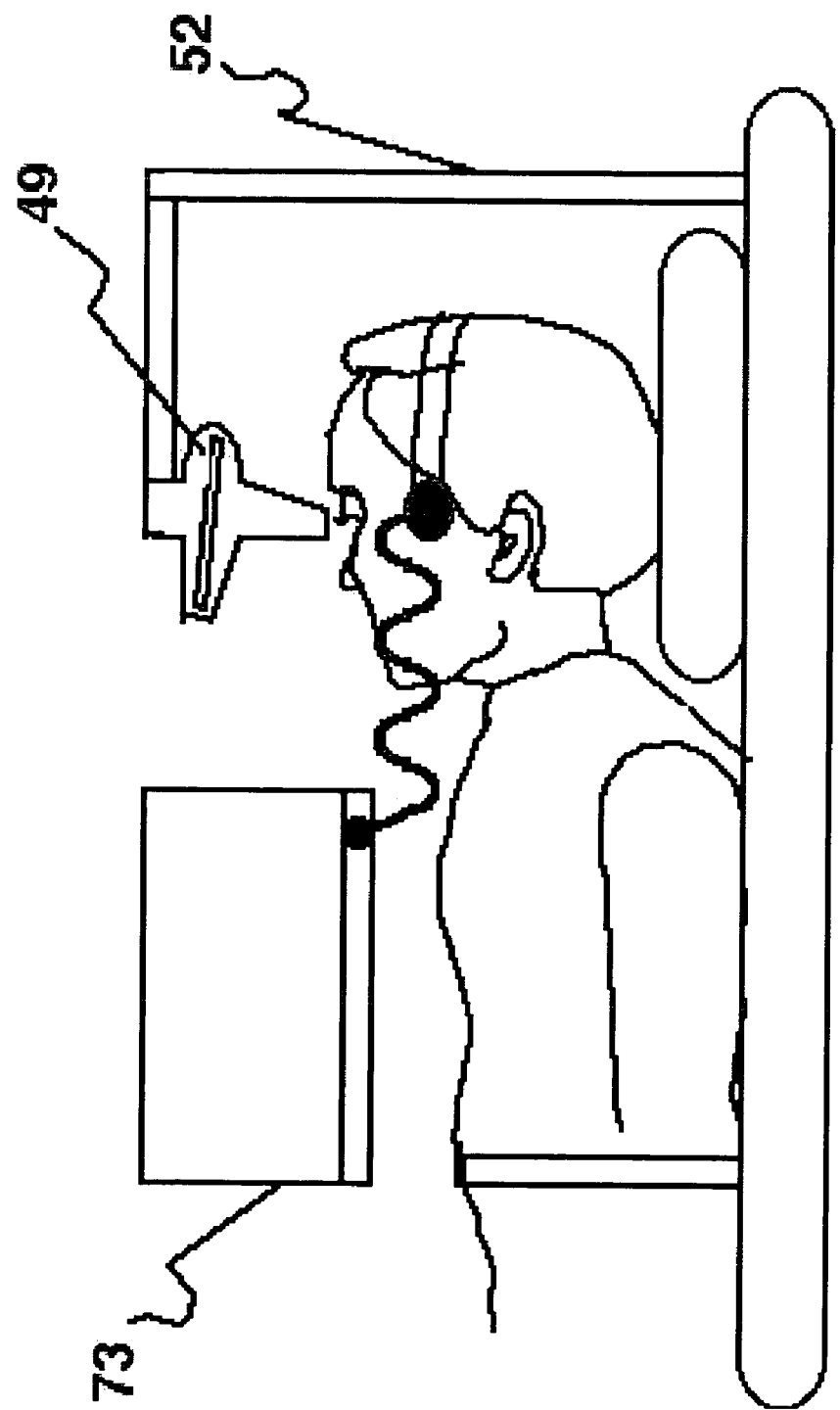

FIG. 11A shows the whole embodiment of the handheld version of the color device and the blood flow velocity monitoring device of the present invention used for a subject in sitting position. The TCD probes (transducer) are fitted on the temples and held in place by a head holder device 70 such as that described in U.S. Pat. No. 6,547,737 to Njemanze. The transducer cord 71 is connected to the TCD device 73 at a port 72. The TCD device via a cord 74 powers the optical circuit that illuminates the right aperture 64 of the color device 49. FIG. 11B shows the whole embodiment of the hands-free version of the color device and the blood now velocity monitoring device of the present invention used for a subject in sitting position. The color device is suspended on a stationary stand 52. FIG. 11C shows the whole embodiment of the handheld version of the color device and the blood flow velocity monitoring device of the present invention used for a subject in lying position. The color device is suspended on a stationary stand 52.

Figure 12:
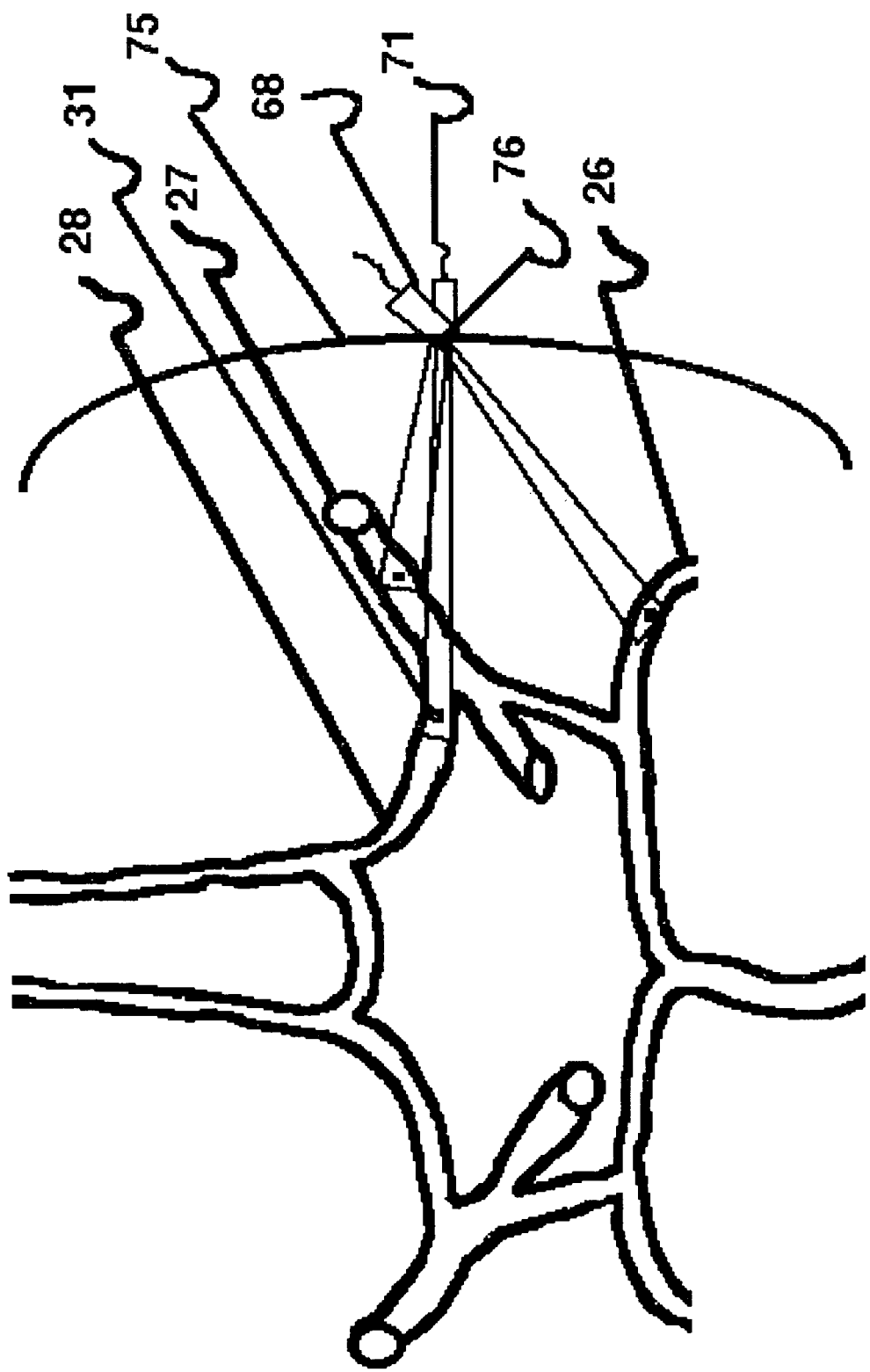
FIG. 12 shows the arteries of the circle of Willis within which ultrasound sample volume is placed for monitoring blood flow velocity changes using the present invention.

FIG. 12 shows the arteries of the circle of Willis within which ultrasound sample volume is placed for monitoring blood flow velocity changes using the present invention. The TCD probe 68 surface is covered with ultrasound gel and placed on the skin over the surface of the temples 69 and angled at the artery of interest through the posterior 75 or middle 76 temporal windows, the ultrasound beam could be directed to the PCA 26, MCA 28 and ACA 31.

Figure 13:
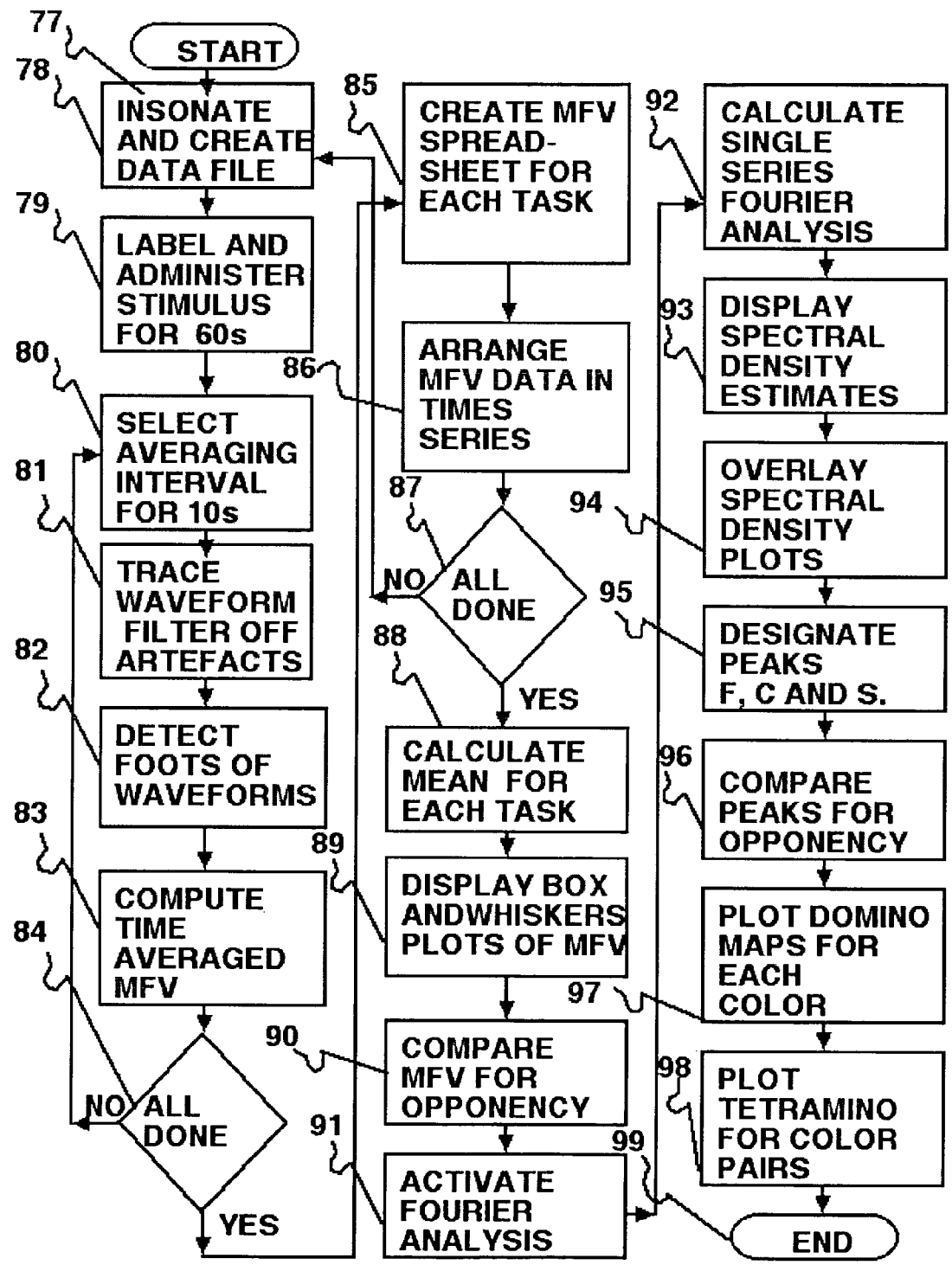
FIG. 13 shows the flow chart for the operation of the blood flow velocity monitoring device of the present invention.

FIG. 13 shows the flow chart for the operation of the blood flow velocity monitoring device of the present invention. Once the subject to be investigated is placed as shown in one of the settings (FIGS. 11A-C), power is connected to the TCD instrument and the operational software is started 77, including means to power the light source of the color device and software means to control an automated switching system for changing as well as labeling the color slides in one embodiment of the invention. The artery of choice is insonated and data files created for the data set 78. The stimulus is administered for a chosen duration for example 60 seconds and labeled 79. The time segment for averaging is chosen for example 10 seconds 80. The program am proceeds to trace the waveform envelopes in the selected time segment and filters off artifacts (waveform distortions) 81. It detects the foot of the first waveform at start and the foot at the end of time interval 82, and computes the time averaged mean flow velocity across that interval and so on for the stimulus duration 83. If all is not computed it goes hack to step 80, but if done, it proceeds to create a spreadsheet for MFV for each stimulus 85. The MIN values for each stimulus are arranged in a time series 86, that is, according to the time of acquisition relative to onset of stimulus for example 0-10 sec, 11-20 sec, 21-30 sec, 31-40 sec, 41-50 sec, and 51-60 sec. When data for all subjects are assembled then it proceeds to calculate mean values and other statistics 88, but if not, it begins at step 78 for the next subject. It plots the mean and whiskers plots 89 of MFV for each stimulus to allow the investigator to evaluate mean values and effects of outliners. In color stimulation, it examines opponent mechanism 90 by comparing effects obtained from blue versus yellow or red versus green or other combinations. It could also use the time series to compute single Fourier analysis using standard statistical module 91 for each stimulus 92 and display the spectral density plots 93. The program overlays the spectral density plots for all stimuli 94 and identifies the fundamental (F-peak), cortical (C-peak) and subcortical (S-peak) 95, the peaks are compared to uncover opponent mechanism 96. If desirable, the program may proceed to represent the determined opponent mechanism at cortical and subcortical regions as dominos 97 and then as tetraminos 98 for opponent color pairs before it ends 99.

The inventor in order to illustrate the use of the invention performed an experiment detailed below. First, a few clarifications on terms and definitions used in the experiment and elsewhere in the present invention: the person being examined is referred to as a subject; the examiner is referred to as an investigator. Mean blood flow velocity measured in the MCA main stem is a direct correlate of cerebral blood flow in that vascular territory. Transcranial Doppler (TCD) ultrasound is used to measure mean blood flow velocity (MFV) in major cerebral arteries in real-time.

Methods

The study included 8 men of mean.+−.SD age of 24.8.+−.2.5 years, all were 100% right handed as determined using the Edinburgh Handedness Inventory as described by Oldfield, R. C. in an article titled "The assessment and analysis of handedness: The Edinburgh inventory," published in Neuropsychologia volume 9, pages 97-114, in 1971. Subjects were all normatensive, systolic 110.+−0.6 mmHg and diastolic 70.+−0.6 mmHg. Visual acuity tested using Snellen's chart, color vision was tested using Ishihara color plates described by Ishihara, S., in an hook titled "Tests for Colour-Blindness," Tokyo, Kanehara Shuppan, 1971, and color recognition were normal as described by Frisen, L., in a book titled "Clinical Tests of Vision." Raven Press, New York, 1990. No subject was on any medication for any disease condition at the time of the study. All subjects were non-smokers and had no history of alcohol abuse, including in their immediate families. All refrained from use of caffeine at least 24-hours prior to testing. All had normal findings for cardiovascular, neurologic and respiratory systems. All maintained the usual restrictions for psychophysiologic studies as described by Stroobant, N. and Vingerhoets, G., in an article titled "Transcranial Doppler ultrasonography monitoring of cerebral hemodynamics during performance of cognitive tasks. A Review." Published in Neuropyschological Review, volume 10, pages 213-231., in 2000. All subjects signed written informed consent according to the Declaration of Helsinki, and the Institutional Review Board approved the study protocol. The TCD scanning procedure was similar to that used in other cognitive studies described by Njemanze P C, Gomez C R and Horenstein S, in an article entitled "Cerebral lateralization and color perception: a transcranial Doppler study," published in a journal Cortex, 1992 volume 28, pages 69-75. Briefly, TCD studies were performed using two 2 MHz probes of a bilateral simultaneous TCD instrument (Multi-Dop T, DWL, Singen, Germany), with sample volume placed in the RMCA and LMCA main stems at a depth of 50 mm. The probes were fixated using the LAM-RAK device (DWL, Singen, Germany) and permitted insonation at the same probe-to-vessel angle at repeated runs for each individual subject. Electrocardiographic and pulse monitoring were performed. Blood pressure measurements were taken before and after testing. Self perceived anxiety level was assessed using a standardized questionnaire before and after testing. Recordings were made with the subject lying supine with head and trunk elevated at 30 degrees.

Tasks and Rationale

The tasks were designed by the author and have demonstrated consistency and reliability with TCD ultrasonography in studies in our laboratory. Briefly, a specially adapted 3D-viewing device (Viewmaster, Portland, Oreg.) was used. The inside of the device was coated with black paint. The right light aperture was covered with dark tape to allow background lighting only through the left. Thus there was a predominant right visual held of view. The rationale was based on the physiology of the visual system. The closure of one visual field was to preclude the effects of binocular interaction due to stereopsis, the perception of depth as described by Gouras, P., in an article titled "Cortical mechanisms of colour vision. In: The Perception of Colour, (Vol. 6), Vision and Dysfunction." Ed: P. Gouras, Macmillan, England, 1991, p. 179-197. It is inappropriate to mix the inputs from both retinas in a single neuron before the information of color vision has been extracted as described by Regan, D., in an article titled "Spatial vision for objects defined by colour contrast, binocular disparity and motion parallax. In: Spatial vision." Ed: D. Regan, London, Macmillan, 1991, 135-178. Furthermore, stimulations were directed at color processing cells receiving inputs from one eye which are usually grouped together within the same area of the striate cortex extending from the upper to the lower cortical layers often referred to as ocular dominance column (blobs) as described by Gouras, P., in an article titled "Cortical mechanisms of colour vision. In: The Perception of Colour, (Vol. 6), Vision and Dysfunction." Ed: P. Gouras, Macmillan, England, 1991; p. 179-197 and in an article by Livingstone, M. S., and Hubel D. H. titled "Anatomy and physiology of a color system in the primate visual cortex." J Neurosci. 4:309-356, 1984, rather than those receiving inputs from both eyes, called hypercolumn as described by Gouras, P., in an article titled "Cortical mechanisms of colour vision. In: The Perception of Colour, (Vol. 6), Vision and Dysfunction." Ed: P. Gouras, Macmillan, England, 1991; p. 179-197.

Optical homogenous filters were placed on the reel (Viewmaster, Portland, Oreg.) of the light path for color stimulation, and open for white light. Kodak Wratten filters: deep Blue (No. 4713), Deep Yellow (No. 12), and Red tricolor (No. 25) were used for light wavelengths ($\lambda$), in the blue (S$\lambda$=452.7 nm), yellow (M$\lambda$=510 nm) and red (L$\lambda$=617.2 nm) wavelength range respectively, as described in Kodak Photographic Filters Handbook. Publication No. B-3., 1990. Rochester, N.Y. Eastman Kodak Company. For each stimulus condition, a continuous train of velocity waveform envelopes was recorded for 60-s simultaneously from the RMCA and LMCA, respectively. The baseline condition was dark resting state, with the subject mute, still and attention focused within the dark visual field with no mental or manual tasks to perform. Studies in dark were used as baseline for lateralization to compare the effect of colors relative to non-spectral stimuli. The condition for data acquisition during visual stimuli presentation was identical to that of baseline except for the color filters and white light.

Calculations

Artifacts of recordings were marked and removed. Velocity waveform envelopes for the relevant 60-s intervals were first averaged in 10-s segments to produce six values for dark condition and each color condition respectively, and were used for further computations of laterality index (LI'). Cerebral lateralization was assessed using LI' expressed as:

LI'=(RMCA MFV 10 s minus LMCA MIN 10 s)/ (RMCA MFV 10 s plus LMCA MIN 10 s))*100.

The relative value of lateralization (LI) for each 10-s segment for each color was calculated as the difference between LI' values measured during the 10-s segment of the color and the corresponding 10-s segment of black baseline condition (onset of black corresponds with onset of color within the 60-s segment):

LI=LI' color 10 s minus LI' black 10 s.

In general, positive LI values suggest right lateralization, while negative LI values suggest tell lateralization. Zero LI values showed no lateralization from baseline or possible bilateral response. LI values calculated for each 10-s segment of the MFV envelope, were used for further analysis.

Statistics. Results were given as mean.+-.SD or mean.+-.SE in box and whiskers plots. Analysis of variance (ANOVA) with repeated measures was performed. All statistical analyses were performed using the software package (Statistica, StatSoft, Okla., USA).

Fourier Analysis

Fourier transform of f(t) requires discrete sample values of f(t), which could be designated as $f_k$. In addition, a computer can compute the transform F(s) only at discrete values of s, that is, it can only provide discrete samples of the transform, $F_r$. If f(kT) and F($rs_0$) are the kth and rth samples of f(t) and F(s), respectively, and $N_0$ is the number of samples in the signal in one period $T_0$, then $$f_k = Tf(kT) = T_0 N_0^{-1} f(kT) \quad (1)$$

and $$Fr = F(rs_0)$$

where $$s_0 = 2\pi T_0^{-1}.$$

The discrete Fourier transform (DFT) is defined as:

$$F_r = \sum_{k=0}^{N_0-1} f_k \exp(-ir\Omega_0 k) \quad (2)$$

where $\Omega_0 = 2\pi N_0^{-1}$

Equations (1) and (2) are used to compute transforms. Fast Fourier transform (FFT) algorithm was applied using standard software (Time series and forecasting module, Statistica for Macintosh, StatSoft, Okla.). The standard and most efficient FFT algorithm requires that the length of the input series is equal to a power of 2. If this is not the case, additional computations have to be performed. The data was averaged in 10 seconds segments for one minute duration, for each stimulus; yielding 6 data points for each subject; and a total of 48 data points each for all eight men and women, respectively. The period of a sine or cosine function is defined as the length of time required for one full cycle, thus it is the inverse of frequency. The sine and cosine functions are independent; thus the periodogram could be determined as a sum of the squared coefficients for each frequency. The frequencies with the greatest spectral densities; that is, the frequency regions, consisting of many adjacent frequencies that contribute most to the overall periodic behavior of the series, for each vessel (RMCA and LMCA, respectively) were determined. This could be accomplished by smoothing the periodogram values via a weighted moving average transformation. Hamming window was applied as a smoother as described by Bloomfield, P., in a hook titled "Fourier analysis of time series. An introduction." New York: Wiley, 1976. The outputs of the time series module of the software selected: frequency, period, cosine and sine coefficients, periodogram values and spectral density estimates. The spectral density estimates derived from single series Fourier analysis, were plotted, and the frequency regions with the highest estimates were marked as peaks. The synchronized periodicities were examined using calculation of cross amplitude. Cross amplitude was computed as the square root of the sum of the squared cross-density and quad-density values. The cross-amplitude was interpreted as a measure of covariance between the respective frequency components of the MFV series for the RMCA and LMCA. The presence of large spectral density estimates for both RMCA and LMCA and the cross-amplitude values at frequencies for the peaks identified, suggest two strong synchronized periodicities in both series at those frequencies during the event-related recording. The values of the cross-amplitudes were only utilized for the purpose of confirming the synchronized peak frequencies, and were not further displayed.

The origin of these peaks could be presumed, from what is known of the anatomy of the vascular system. It is known that, a major proximal reflection site relative to recording site at the main stem of the MCA, would arise close to the aortic bifurcation as described by McDonald, D. A., in a book titled "Blood Flow in Arteries." Baltimore: Williams and Wilkins Co. pp. 311-350, 1974, and also from the finger tips as described by Njemanze P C titled "Cerebral lateralization for facial processing: Gender-related cognitive styles determined using Fourier analysis of mean cerebral blood flow velocity in the middle cerebral arteries," published in the journal Laterality, 2007, volume 12, pages 31-49; while the distal sites would emanate from the cortical and ganglionic terminal vessels. These three terminal sites would have the corresponding peaks designated as F-peak, S-peak and C-peak, respectively. The F-peak is the fundamental frequency of cardiovascular oscillation. The S-peak is designated as the subcortical peak that would be presumed to arise at subcortical sites. While the C-peak is designated the cortical peak, that would be presumed to arise at cortical sites. For comparison, plots for baseline (dark) and each paradigm were copied and then overlaid, on the same scale for frequency and spectral density estimates using a graphic software (Adobe Photoshop 7.0, Adobe, San Jose, Calif.).

Reflection Sites and Arterial Length

It could be considered that the fundamental frequency F-peak represents the first harmonic of the cardiovascular oscillation. The $2^{nd}$ and $3^{rd}$ harmonics, occur at twice and thrice the frequency of the first, and may indicate distal reflections from the cortical and ganglionic (subcortical) vessels respectively. The distance (L), of the reflection site from measurement point, could be estimated given the frequency of the harmonic f, and the arterial pulse wave velocity (aPWV) (c). The presumed reflection site is given by (L=c/f) as described by McDonald, D. A., in a book titled "Blood Flow in Arteries." Baltimore: Williams and Wilkins Co. pp. 311-350, 1974. Therefore, the putative reflection sites for the $1^{st}$ harmonic, would be at $L_1=\frac{1}{4}\lambda$ or c/4 f; the $2^{nd}$ harmonic, at $L_2=\frac{1}{8}\lambda$ or c/8×2 f and $3^{rd}$ harmonic, at $L_3=\frac{1}{16}\lambda$ or c/16×3 f. In human carotid-femoral vessels, several estimates put aPWV at c=6.15 msec$^{-1}$ as described by Taniwaki, H., Kawagishi, T., Emoto, M., Shoji, T., Kanda, H., Maekawa, K., Nishizawa, Y. and Morii H., in an article titled "Correlation between the intima-media thickness of the carotid artery and aortic pulse-wave velocity in patients with type 2 diabetes. Vessel wall properties in type 2 diabetes." published in Diabetes Care, volume 22, pages 1851-1857 in 1999; and in the common carotid artery, c=5.5±1.5 msec$^{-1}$ as described by Winders, J. M. Kornet, L., Brands, P. J., and Hocks, A. P., in an article titled "Assessment of local pulse wave velocity in arteries using 2D distension waveforms." published in Ultrasonography Imaging, volume 23, pages 199-215, in 2001. The estimated distance may not correlate with known morphometric dimensions of the arterial tree as described by Campbell, K. B., Lee, L. C., Frasch, H. F., and Noordergraaf, A., in an article titled "Pulse reflection sites and effective length of the arterial system." published in American Journal of Physiology, volume 256, pages H1684-H1689 in 1989.

Results

Figure 14:
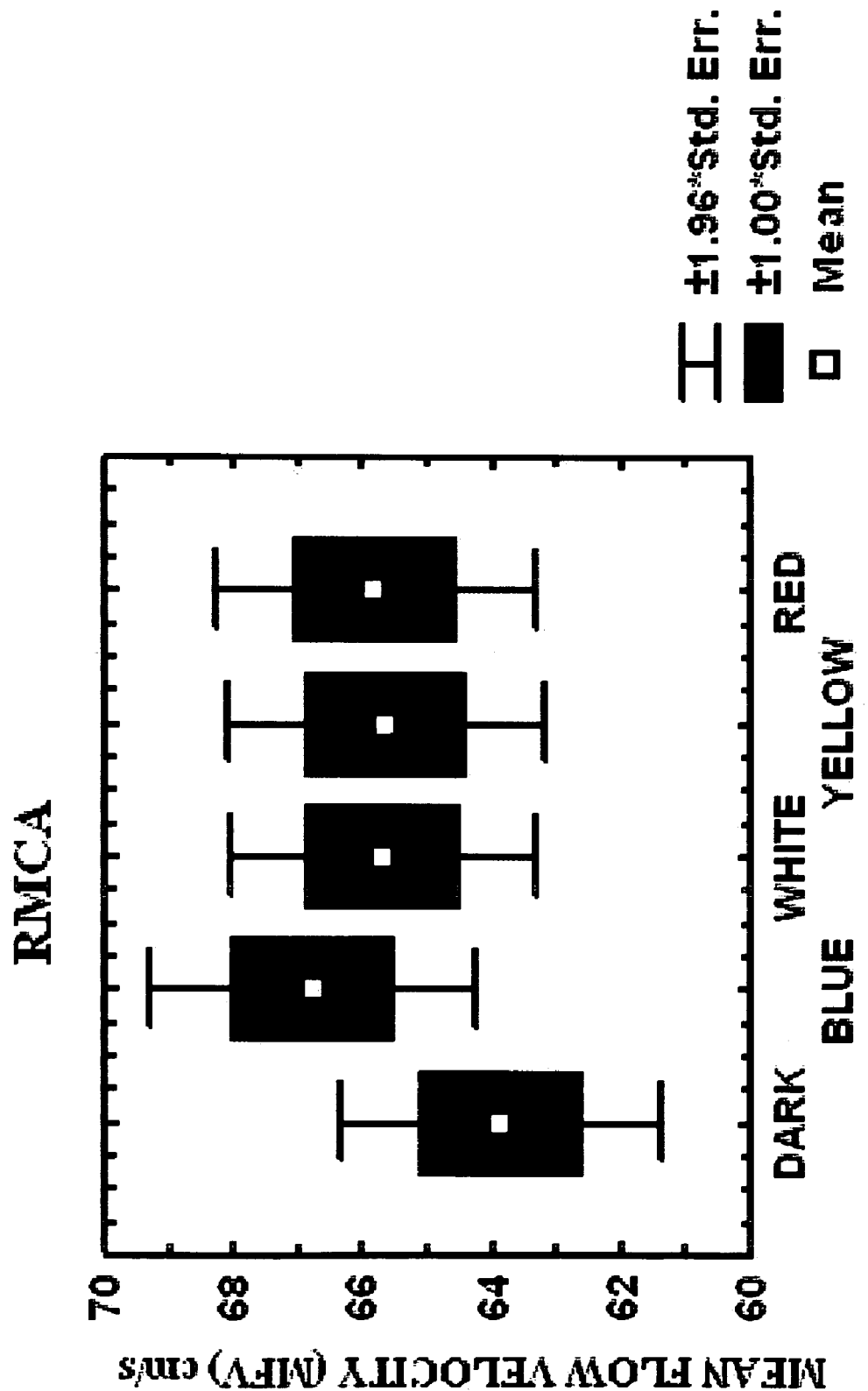
FIG. 14A shows the box and whiskers plots of mean flow velocity in the RMCA obtained for dark, blue, white and yellow stimulations.
FIG. 14B shows the box and whiskers plots of mean flow velocity in the LMCA obtained for dark, blue, white and yellow stimulations.
FIG. 14C shows the box and whiskers plots of laterality index obtained for dark, blue, white and yellow stimulations.
Figure 14:
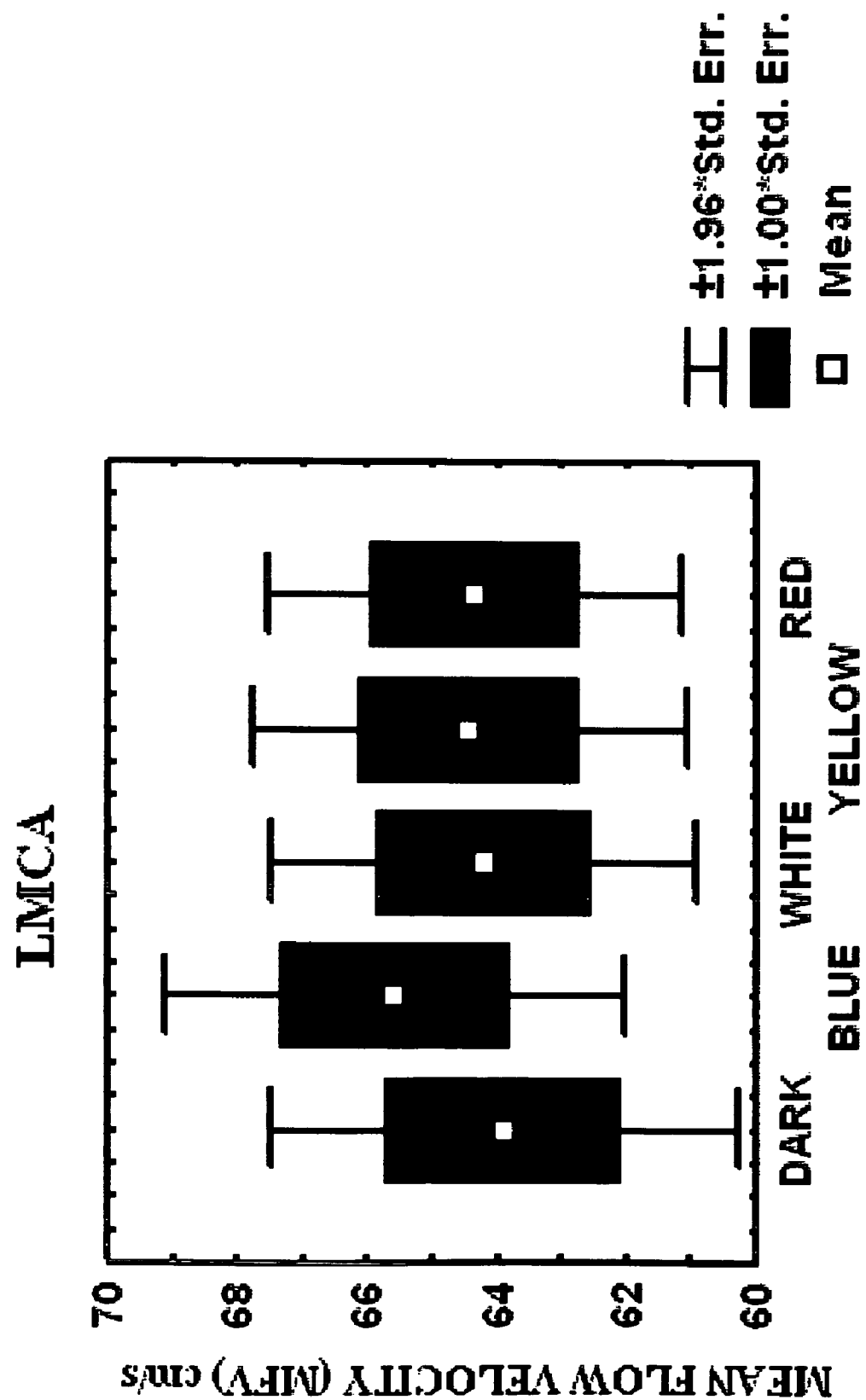
Figure 14:
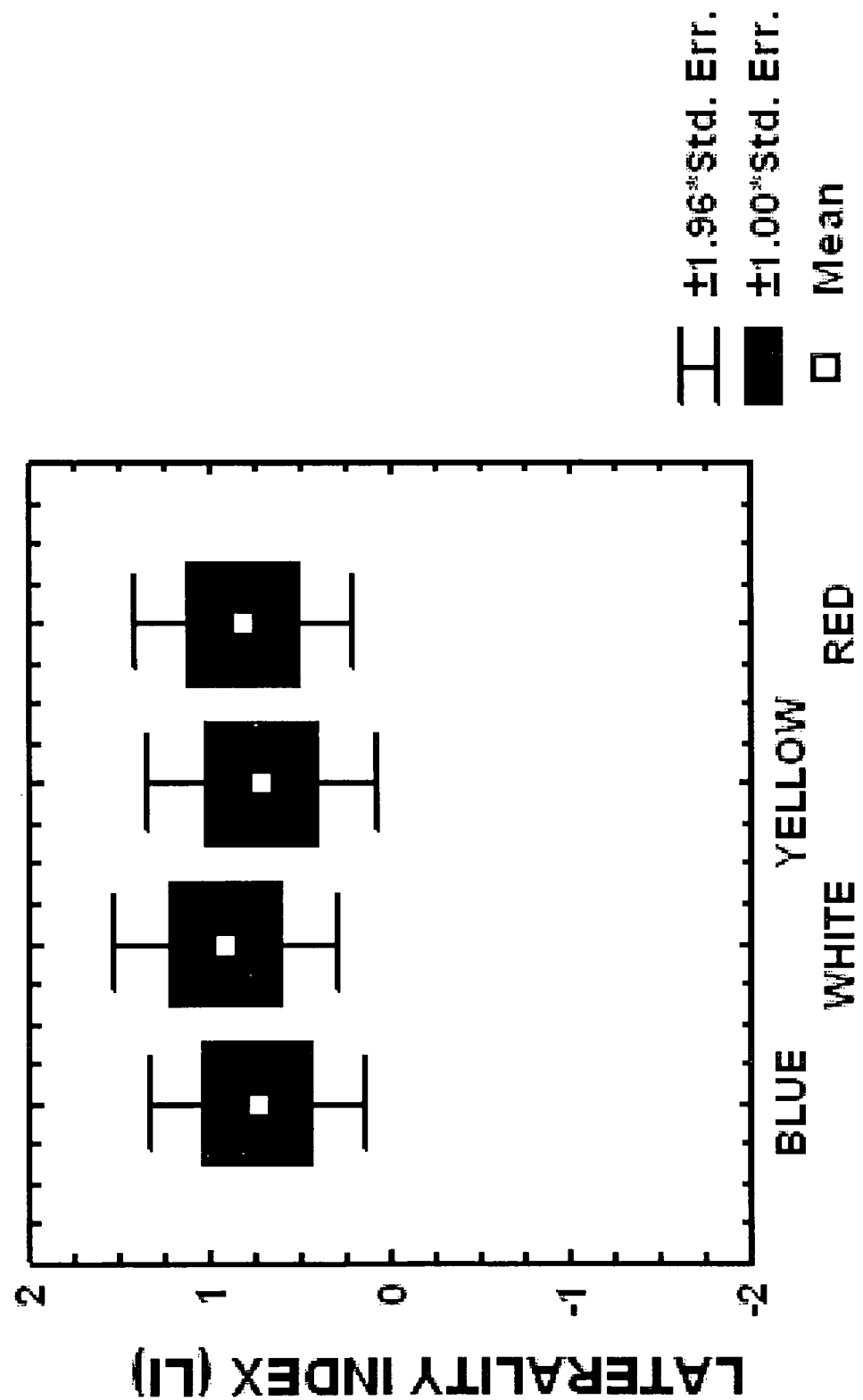

FIG. 14A shows the box and whiskers plots of mean flow velocity in the RMCA obtained for dark, blue, white and yellow stimulations. The luminance effect (dark versus white) was significant $F(1,47)=6.1$, $p<0.05$. The opponent mechanisms for blue versus yellow was marginally significant $F(1,47)=3.8$, $p=0.058$. FIG. 14B shows the box and whiskers plots of mean flow velocity in the LMCA obtained for dark, blue, white and yellow stimulations. There was no luminance effect (p=NS) and opponent mechanism for blue versus yellow was absent (p=NS). FIG. 14C shows the box and whiskers plots of laterality index showing right lateralization for all color stimuli.

Figure 15A:
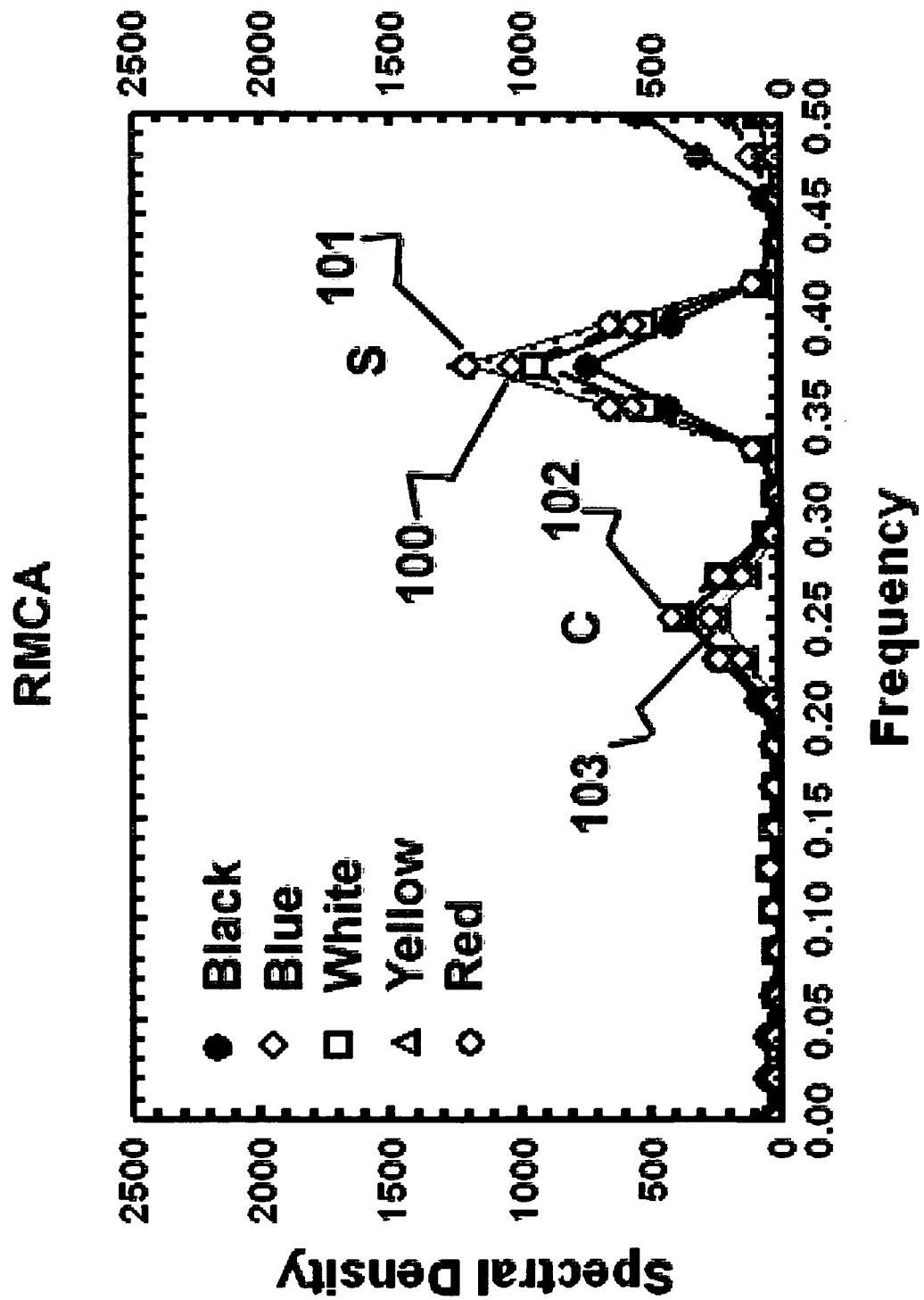
FIG. 15A shows the spectral density plots for the RMCA of healthy male subjects and displaying color (blue versus yellow) opponent processing at cortical (C-peaks) and subcortical (S-peaks) obtained using the present invention.
Figure 15:
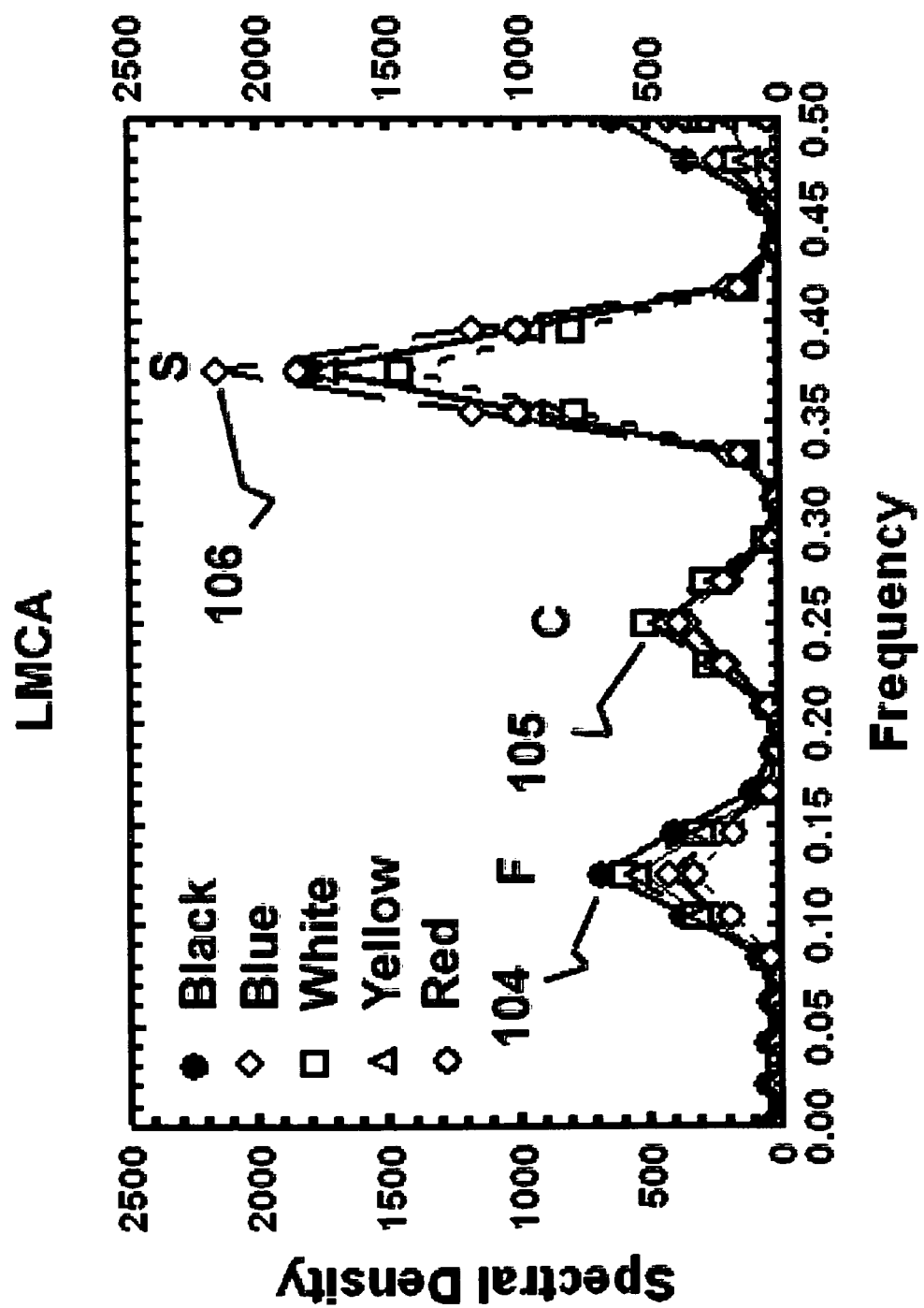
FIG. 15B shows the spectral density plots for the LMCA of healthy male subjects and displaying the fundamental (F-peaks), cortical (C-peaks) and subcortical (S-peaks) for the different stimuli obtained using the present invention.

FIG. 15A shows the spectral density plots for the RMCA of healthy male subjects and displaying color (blue versus yellow) opponent processing at cortical (C-peaks) and subcortical (S-peaks) obtained using the present invention. The F-peaks were not visible when reflections from the finger tips are blocked by flexion of the elbow joint while subjects held the hand-held version of the color device. The subcortical S-peaks for colors were accentuated than dark. The S-peaks were grouped into lower peak for short wave (blue) 100 and higher peaks for medium (yellow) and long waves (red) 101. In other words, the subcortical regions showed a spatial organization of processing neuronal cell population with color regions extending from dark into short wave, medium wave and long wave, that is, there is a spectral topology. The cortical C-peaks on the other hand, showed accentuation for short wave (blue) 102, but attenuation for medium (yellow) and long wave (red) responses 103. The latter suggests a reversed spectral topology to that at subcortical region. It could be proposed that spectral and spatial opponency necessary for simultaneous color contrast is achieved by reversed spectral topology at cortical region compared to that at subcortical region.

FIG. 15B shows the spectral density plots for the LMCA of healthy male subjects and displaying the fundamental (F-peaks), cortical (C-peaks) and subcortical (S-peaks) for the different stimuli obtained using the present invention. The F peaks 104 are seen if subjects stretched the left arm and hand. The C-peaks and S-peaks did not show opponent mechanism.

Figure 16:
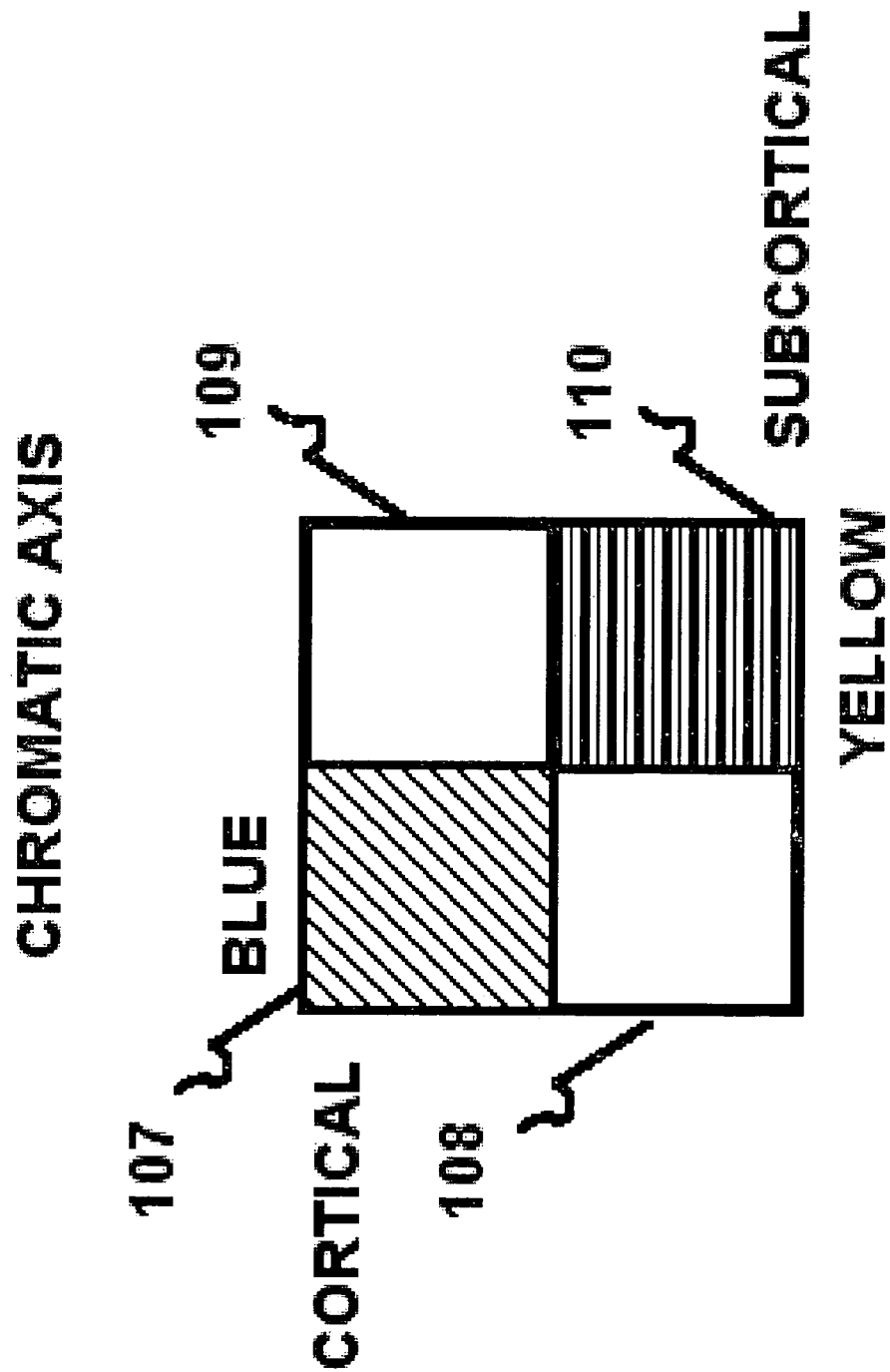
FIG. 16A shows the tetraminos for blue-yellow chromatic contrast opponent mechanism derived from spectral density plots for cortical and subcortical activities obtained using the present invention.
FIG. 16B shows the tetraminos for black-white luminance contrast derived from spectral density plots of cortical and subcortical activities obtained using the present invention.
Figure 16:
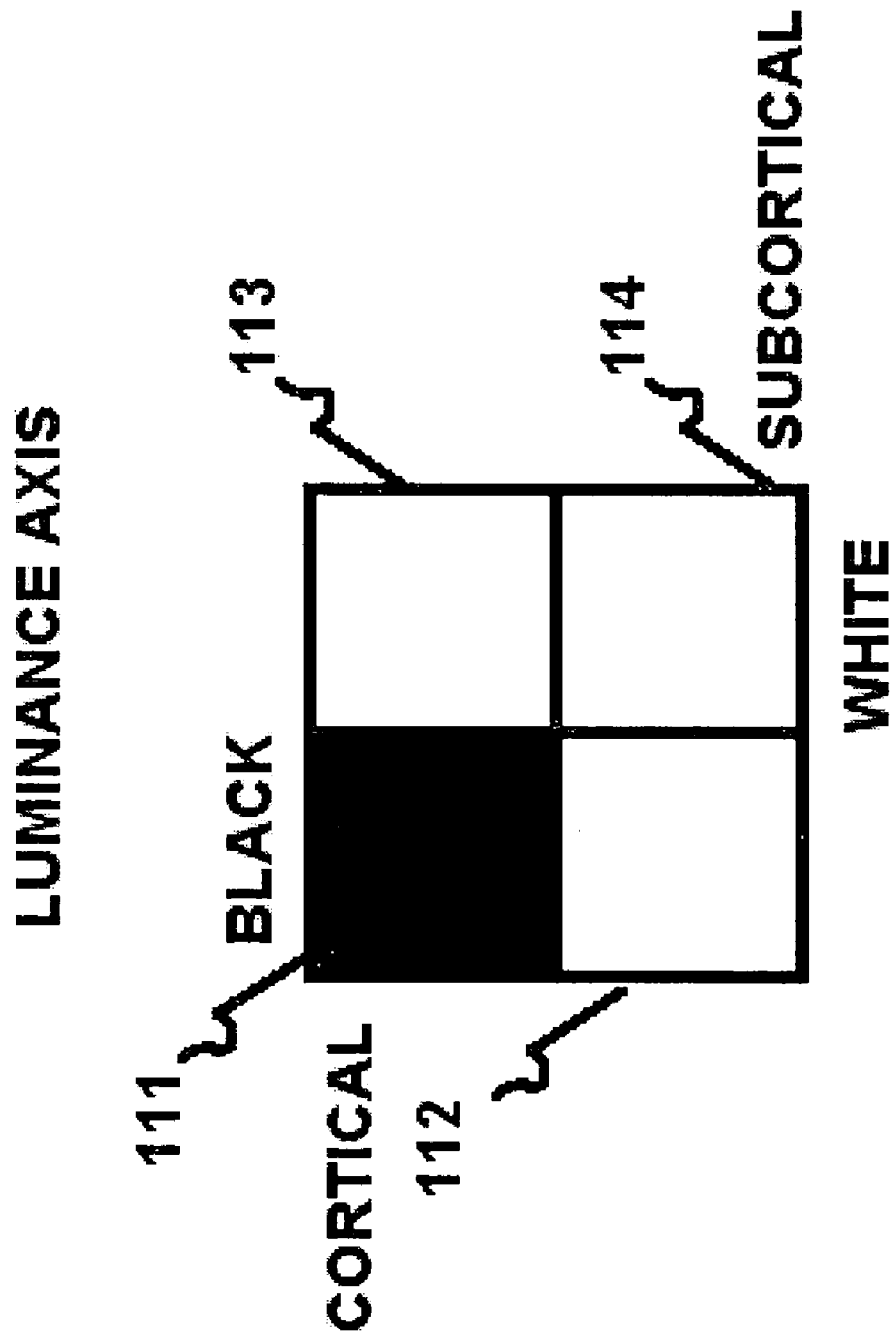

FIG. 16A shows the tetramino for blue-yellow chromatic contrast opponent mechanism derived from spectral density plots for cortical and subcortical activities obtained using the present invention. The tetramino is a simplified representation of opponent mechanism in the different vascular territories allowing easy comparison among large study cohorts. The chromatic axis and luminance axis are represented by each tetramino or double dominos, respectively. The chromatic axis for short wave (blue) is shown in the first row, while in the second row the medium (yellow) or long wave (red) is shown. The activation in the cortical region is shown in the first column, while the activation in the subcortical region is shown in second column of the tetramino. The accentuated response is represented by paved domino and unpaved domino represents the attenuated response. As aforementioned (FIG. 15A), the paved domino for blue 107 shows accentuated response at cortical C-peak but attenuation at subcortical peak (unpaved domino) 108. At the cortical C-peak for yellow there was attenuation shown as unpaved domino 109, but accentuation at subcortical S-peak shown by paved domino 110. FIG. 16B shows the tetraminos for black-white luminance contrast derived from spectral density plots of cortical and subcortical activities obtained using the present invention. Similarly, for the luminance axis, black is shown in the first row and white is shown in the second row. The response to black was accentuated at the cortical C-peak and shown as paved domino 111 but attenuated at the subcortical S-peak shown as unpaved domino 112. The response to white was attenuated at the cortical C-peak and was shown as unpaved domino 113, but accentuated at the subcortical S-peak shown as paved domino 114.

While the preferred embodiment of the present invention is described above, it is contemplated that various modifications may be made thereto for particular applications without departing from the concept and scope of the present invention. Accordingly, the scope of the present invention should not be limited by the example described thereto but be determined by reference to the claims hereinafter provided.

What is claimed is:

1. A noninvasive method to determine the cerebral blood flow velocity response to colors of light observed by a human subject, including steps of: (a) obtaining a subject's baseline mean blood flow velocity in cerebral arteries on both sides of the brain using a simultaneous transcranial Doppler instrument with two probes placed on the temples and sample volumes focused on cerebral arteries on both sides; (b) testing the subject in one visual field with several colors while simultaneously monitoring the mean blood flow velocity in real-time; (c) simultaneously with (b) determining if there is an opponent mechanism between short wavelength and long wavelength colors; (d) simultaneously with (c) determining if there is an opponent mechanism between medium wavelength and long wavelength colors; (e) determining the opponent response between short- and long-wavelength colors using Fourier derived spectral density peaks at cortical and subcortical regions; (f) simultaneously with (e) determining opponent response between short wavelength and long wavelength colors for different vascular territories; (g) representing in a pattern the opponent response in all vascular territories; (h) simultaneously with (g) comparing the opponent response pattern to known patterns in normal and disease conditions; (i) determining regions of abnormal opponent responses; and (j) selecting the wavelength of colors that induced the activation or inhibition of blood flow velocity in areas of abnormal responses.

2. The method of claim 1, further comprising using an abnormal opponent response to determine impaired spectral absorption of the R receptor photopigment (protanomalous trichromat) or of the G receptor photopigment (deuteranomalous trichromat).

3. The method of claim 1, further comprising using an abnormal opponent response to determine impairment of color perception following a hemispheric lesion or central dyschromatopsia.

4. The method of claim 1 wherein cerebral blood flow velocity is obtained as a measurement by using a microcomputer in said transcranial Doppler instrument powered from an electrical source.

5. The method of claim 1, wherein said determining of the opponent response between short- and long-wavelength colors using Fourier derived spectral density peaks is performed by using software for statistical computation of said mean flow velocity values.

6. The method of claim 1 wherein said testing of the subject with several colors while simultaneously monitoring the mean blood flow velocity in real-time is performed by using said transcranial Doppler instrument in operative connection with a color device for presenting said colors.

7. The method of claim 1 further including testing the subject with several colors which are each matched to measure mean blood flow velocity in real-time and wherein the several colors are provided to the visual field of the subject by using a device having a switching system in order to change and label the color filters which are mounted on a reel.

8. The method of claim 1 wherein said step of determining if there is an opponent mechanism between short wavelength and long wavelength colors is performed using software, and plotting and analysis is made of the opponent mechanisms in tetraminos for each color pair in each vascular territory.

9. The method of claim 1 wherein said step of selecting a wavelength or wavelengths of color which will induce activation or inhibition of blood flow velocity as a desirable effect is performed by using a wavelength selecting device, said method further comprising the step of determining spectrophotometric parameters for color filters which have said desirable effect on cerebral blood flow.

10. A noninvasive method to determine the cerebral blood flow velocity response to colors of light observed by a human subject, including steps of: (a) obtaining a subject's baseline mean blood flow velocity in cerebral arteries on both sides of the brain using a simultaneous transcranial Doppler instrument with two probes placed on the temples and sample volumes focused on cerebral arteries on both sides; (b) testing the subject with several colors while simultaneously monitoring the mean blood flow velocity in real-time; (c) simultaneously with (b) presenting light only through the left visual field to stimulate only the right visual cortex and pathways; (d) simultaneously with (c) while the right visual field is blocked with a dark slide; (e) determining the response of the brain to colors of different wavelengths using mean blood flow velocity; (f) simultaneously with (e) determining if there is an opponent mechanism between short wavelength and long wavelength colors; (g) simultaneously with (f) determining if there is an opponent mechanism between medium wavelength and long wavelength colors; (h) determining the opponent response between short wavelength and long wavelength colors using Fourier derived spectral density peaks at cortical and subcortical regions; (i) simultaneously with (h) determining opponent response between short wavelength and long wavelength colors for different vascular territories; (j) representing the opponent response in a pattern of dominos and tetraminos for all vascular territories; (k) simultaneously with (j) comparing the opponent response pattern to known patterns in normal and disease conditions; (l) determining regions of abnormal opponent responses; (m) selecting the wavelength of colors that induce the activation or inhibition of blood flow velocity in areas of abnormal responses; (n) determining the spectrometric parameters of the color filters found to have desirable effects on cerebral blood flow; and (o) using the physical parameters to manufacture color filters such as contact lens and special spectacles.

11. The method of claim 10, further comprising the step of using said color filters for diagnosing patients with a variety of brain disease conditions.

12. The method of claim 10, further comprising the step of using said color filters for diagnosing and treating patients with sleep disorders.

13. The method of claim 10, further comprising the step of using said color filters for diagnosing and treating effects of adaptational neuroplasticity in special environments.

14. The method of claim 10, further comprising the step of using color filters for diagnosing and treating disorders of the immune system and infectious diseases.

* * * * *